United States Patent [19]
Ries et al.

[11] Patent Number: 5,270,322
[45] Date of Patent: Dec. 14, 1993

[54] IMIDAZO[1,2-A]PYRIDINES, PHARMACEUTICAL COMPOSITIONS CONTAINING THESE COMPOUNDS AND PROCESSES FOR PREPARING THEM

[75] Inventors: Uwe Ries, Biberach; Norbert Hauel, Schemmerhofen; Berthold Narr, Biberach; Jacques van Meel, Mittelbiberach; Wolfgang Wienen, A fingen; Michael Entzeroth, Warthausen, all of Fed. Rep. of Germany

[73] Assignee: Dr. Karl Thomae GmbH, Biberach an der Riss, Fed. Rep. of Germany

[21] Appl. No.: 15,508

[22] Filed: Feb. 9, 1993

[30] Foreign Application Priority Data

Feb. 11, 1992 [DE] Fed. Rep. of Germany ....... 4203872

[51] Int. Cl.$^5$ ................... A61K 31/435; C07D 471/04
[52] U.S. Cl. ..................................... 514/300; 514/80; 546/23; 546/121; 546/118; 544/236; 544/277; 544/350
[58] Field of Search .................... 546/121, 23; 514/80, 514/300

[56] References Cited
PUBLICATIONS
Thomas et al., J. Med. Chem., vol. 35, pp. 877–885 (1992).

Primary Examiner—Bernard Dentz
Attorney, Agent, or Firm—David E. Frankhouser; Alan R. Stempel; Mary-Ellen M. Timbers

[57] ABSTRACT

Imidazo[1,2-a]pyridines of the formula

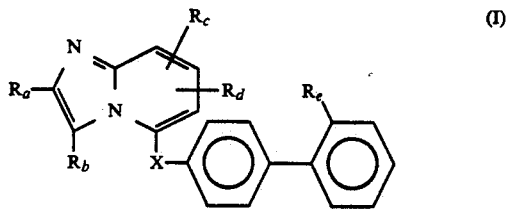

wherein $R_a$ to $R_e$ are as defined herein, the enantiomers and the salts thereof, which are useful as angiotensin antagonists and for treating conditions treatable with angiotensin antagonists.

12 Claims, No Drawings

IMIDAZO[1,2-A]PYRIDINES, PHARMACEUTICAL COMPOSITIONS CONTAINING THESE COMPOUNDS AND PROCESSES FOR PREPARING THEM

The present invention relates to new imidazo[1,2-a]pyridines of general formula

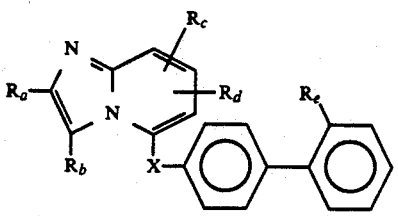

the enantiomers and the salts thereof, particularly, for pharmaceutical use, the physiologically acceptable salts thereof with inorganic or organic acids or bases.

In general formula I above $R_a$ denotes a straight-chained or branched $C_{1-6}$-alkyl group, a cycloalkyl group, an alkyl group substituted by an alkoxy group, or a $C_{1-4}$-alkoxy group, $R_b$ denotes a hydrogen, fluorine, chlorine or bromine atom, or an alkyl, hydroxymethyl, trifluoromethyl, formyl, carboxy, alkoxycarbonyl, cyano, nitro, $NH_2CH_2$—, $R_1NHCH_2$— or $R_1NR_2CH_2$— group, wherein $R_1$ and $R_2$, which may be identical or different, denote $C_{1-6}$-alkyl groups, cycloalkyl, cycloalkylalkyl, phenyl or phenylalkyl groups or $R_1$ and $R_2$ together denote a $C_{4-6}$-n-alkylene group, $R_c$ denotes a hydrogen, fluorine, chlorine or bromine atom, an alkyl group optionally substituted by an alkoxy or phenylalkoxy group, an alkoxy, phenylalkoxy, trifluoromethyl, $H_2N$—, $R_1NH$— or $R_1NR_2$— group, wherein $R_1$ and $R_2$ are as hereinbefore defined, $R_d$ denotes a hydrogen atom or an alkyl group, $R_e$ denotes a carboxy group, a group which may be converted in vivo into a carboxy group, or a cyano, 1H-tetrazolyl, 1-triphenylmethyl-tetrazolyl, alkanesulphonylaminocarbonyl, phenylsulphonylaminocarbonyl, phenylalkanesulphonylaminocarbonyl, trifluoromethanesulphonylaminocarbonyl, phosphino, O-alkyl-phosphino, O-aralkyl-phosphino, phosphono, O-alkyl-phosphono, O-aralkyl-phosphono, O,O-dialkylphosphono, phosphono-methyl, O-alkyl-phosphonomethyl, O-aralkyl-phosphono-methyl, O-aryl-phosphonomethyl, O,O-dialkyl-phosphono-methyl, phosphato, O-alkylphosphato, O-aralkyl-phosphato, O-arylphosphato-or O,O-dialkyl-phosphoryl group, X denotes an oxygen atom, an imino group optionally substituted by a formyl, $R_1$— or $R_1CO$— group, or a —CO—, —(HON=C)— or —($R_3CR_4$)— group, wherein $R_3$ is a hydrogen atom or an alkyl group and $R_4$ is a hydrogen atom, an alkoxy group substituted by a carboxy, alkoxycarbonyl, aminocarbonyl, alkylaminocarbonyl, dialkylaminocarbonyl or heteroaryl group, wherein the heteroaryl group is linked to the alkoxy group via a carbon-carbon bond, an alkoxy group substituted in the 2, 3 or 4-position by a heteroaryl group, wherein the heteroaryl group is linked to the alkoxy group via a carbon-nitrogen bond, a hydroxy, dialkylphosphonomethoxy, azido, CHO—O—, $R_1O$—, $R_5NR_6$—, $R_1CO$—O—, $R_1O$—CO—O—, CHO—$NR_5$—, $R_1$—CO—$NR_7$—, $R_1O$—CO—$NR_5$—, $R_5NR_6$—CO—O—, $R_1SO_2$—O—, $R_5NR_6$—CO—$NR_5$— or $R_1SO_2$—$NR_7$— group or $R_3$ and $R_4$ together denote a 1,2-ethylenedioxy- or 1,3-n-propylenedioxy group, wherein in the above-mentioned groups, $R_1$ is as hereinbefore defined, $R_5$ and $R_6$, which may be identical or different, represent hydrogen atoms or have the meanings given for $R_1$ and $R_2$ hereinbefore, $R_7$ denotes a hydrogen atom or an alkyl group or $R_1$ and $R_7$ together denote a $C_{3-5}$-n-alkylene group, whilst unless otherwise specified an alkyl or alkoxy moiety mentioned above may contain 1 to 4 carbon atoms and a cycloalkyl moiety mentioned above may contain 3 to 7 carbon atoms, and the term "an aryl group" denotes a phenyl group optionally mono or disubstituted by a fluorine, chlorine or bromine atom, or by a hydroxy, alkyl, alkoxy, phenylalkoxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylaminosulphonyl or dialkylaminosulphonyl group, wherein each alkyl moiety may contain 1 to 4 carbon atoms, or a naphthyl group, and the term "heteroaryl group" denotes a 5-membered heteroaromatic ring, bound via a carbon atom or an imino group, and containing an imino group, an oxygen or sulphur atom, or an imino group and an oxygen, sulphur or nitrogen atom, or denotes a 6-membered heteroaromatic ring bound via a carbon atom and containing 1 or 2 nitrogen atoms, whilst the above-mentioned heteroaromatic rings may be substituted in the carbon skeleton by a $C_{1-6}$-alkyl group or by a phenylalkyl group and there may be attached to both the 5-membered and to the 6-membered heteroaromatic rings, in each case via two adjacent carbon atoms, an n-propylene, n-butylene or 1,3-butadienyl group or, via an imino group and an adjacent carbon atom, an n-butylene or 1,3-butadienyl group, and in an anellated pyridine ring thus formed a methine group may be replaced by a nitrogen atom and a vinylene group in the 3-, 4-position relative to the nitrogen atom of the pyridine ring formed may be replaced by a sulphur atom or in an anellated phenyl ring thus formed one or two methine groups may be replaced by N-atoms, whilst additionally the above-mentioned fused-on aromatic or heteroaromatic rings in the carbon skeleton may be monosubstituted by a fluorine, chlorine or bromine atom, or by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, fluoromethyl, difluoromethyl, trifluoromethyl, alkanoyl, aminosulphonyl, alkylaminosulphonyl or dialkylaminosulphonyl group or disubstituted by fluorine or chlorine atoms or by methyl, methoxy or hydroxy groups, and two methyl substituents in the 1,2-position relative to one another may be linked to one another by a methylene or ethylene bridge and an NH- group optionally present in an imidazole ring may be substituted by a $C_{1-6}$-alkyl group, by a phenylalkyl group or by a cycloalkyl group.

The new compounds of general formula I above wherein $R_e$ denotes a tert.-butoxycarbonyl, cyano or 1-triphenylmethyl-tetrazolyl group, are valuable intermediate products and the other compounds of general formula I above and the physiologically acceptable salts thereof have valuable pharmacological properties, since they are angiotensin-antagonists, particularly angiotensin-II-antagonists.

The present invention thus relates to the new abovementioned imidazo[1,2-a]pyridines as well as new pharmaceutical compositions which contain one of the above-mentioned pharmacologically active compounds of general formula I or a corresponding physiologically acceptable salt, and are suitable particularly for the treatment of hypertonia and cardiac insufficiency and also for treating ischaemic peripheral circulatory disorders, myocardial ischaemia (angina) and for preventing the progression of cardiac insufficiency after myocardial infarct, for treating diabetic nephropathy, glaucoma, gastrointestinal diseases and bladder diseases.

As examples of the definitions of groups $R_a$ to $R_e$ and $R_1$ to $R_7$ given hereinbefore, $R_a$ may denote, for example, a methyl, ethyl, n-propyl, isopropyl, n-butyl, isobutyl, tert.-butyl, n-pentyl, isopentyl, neopentyl, n-hexyl, isohexyl, 1,1-dimethylbutyl, 2,2-di-methyl-butyl, 3,3-dimethyl-butyl, cyclopropyl, cyclobutyl, cyclopentyl, cyclohexyl, cycloheptyl, methoxy-methyl, 2-methoxy-ethyl, 3-methoxy-n-propyl, ethoxy-methyl, 2-ethoxy-ethyl, 3-ethoxy-n-propyl, n-propyloxy-methyl, 2-(n-propyloxy)ethyl, 3-(n-propyloxy)-n-propyl, isopropyloxy-methyl, 2-isopropyloxyethyl, 3-isopropyloxy-n-propyl, methoxy, ethoxy, n-propyloxy, isopropyloxy-, n-butyloxy-, isobutyloxy- or tert.butyloxy group, $R_b$ may denote a hydrogen, fluorine, chlorine or bromine atom, a cyano, nitro, formyl, carboxy, methoxycarbonyl, ethoxycarbonyl, n-propoxycarbonyl, isopropoxycarbonyl, n-butoxycarbonyl, isobutoxycarbonyl, tert.butoxycarbonyl, trifluoromethyl, methyl, ethyl, n-propyl, isopropyl, hydroxymethyl, aminomethyl, dimethylaminomethyl, diethylaminomethyl, di-n-propylaminomethyl, diisopropylaminomethyl, di-n-butylaminomethyl, diisobutylaminomethyl, (pyrrolidin-1-yl)-methyl, (piperidin-1-yl)-methyl or morpholinomethyl group, $R_c$ may denote a hydrogen, fluorine, chlorine or bromine atom, a methoxy, ethoxy, n-propyloxy, isopropyloxy, benzyloxy, 2-phenylethyloxy, 3-phenyl-n-propyloxy, methyl, ethyl, n-propyl, isopropyl, methoxymethyl, 2-methoxy-ethyl, ethoxymethyl, 2-ethoxyethyl, n-propyloxymethyl, 2-(n-propyloxy)ethyl, isopropyloxymethyl, benzyloxymethyl, 2-benzyloxyethyl, 2-phenylethyloxymethyl, trifluoromethyl, dimethylamino, diethylamino, di-n-propylamino, diisopropylamino, pyrrolidin-1-yl or piperidin-1-yl group, $R_d$ may denote a hydrogen atom, a methyl, ethyl, n-propyl, isopropyl, n-butyl, isobutyl or tert.butyl group, $R_e$ may denote a carboxy, methoxycarbonyl, ethoxycarbonyl, n-propyloxycarbonyl, isopropyloxycarbonyl, n-butyloxycarbonyl, isobutyloxycarbonyl, tert.butyloxycarbonyl, n-pentyloxycarbonyl, n-hexyloxycarbonyl, benzyloxycarbonyl, 1-henylethoxycarbonyl, 2-phenylethoxycarbonyl, 3-phenylpropyloxycarbonyl, acetoxymethyloxycarbonyl, propionyloxymethoxycarbonyl, n-butyryloxymethoxycarbonyl, isobutyryloxymethoxycarbonyl, 1-(acetyloxy)ethoxycarbonyl, 1-(isobutyryloxy)ethoxycarbonyl, benzoyloxymethoxycarbonyl, cinnamyloxycarbonyl, pivaloyloxymethoxycarbonyl, 1-(ethoxycarbonyloxy)-ethoxycarbonyl, methoxymethoxycarbonyl, cyclohexyloxycarbonylmethoxycarbonyl, 1-(cyclohexyloxycarbonyloxy)ethoxycarbonyl, cyclopentylcarbonyloxymethoxycarbonyl, (1,3-dioxa-2-oxo-4-methyl-cyclopenten-5-yl)methoxycarbonyl, cyano, 1H-tetrazolyl, 1-triphenylmethyltetrazolyl, methylsulphonylamino-carbonyl, ethylsulphonylaminocarbonyl-, n-propylsulphonylamino inocarbonyl, isopropylsulphonyl-aminocarbonyl, phenylsulphonylaminocarbonyl, benzylsulphonylaminocarbonyl, 1-phenylethylsulphonylaminocarbonyl, 2-phenylethylsulphonylaminocarbonyl, 1-phenyl-n-propylsulphonylaminocarbonyl, 2-phenyl-n-propylsulphonylaminocarbonyl, 3-phenyl-n-propylsulphonylaminocarbonyl, trifluoromethanesulphonylaminocarbonyl, phosphino, O-methyl-phosphino, O-ethyl-phosphino, O-n-propylphosphino, O-isopropyl-phosphino, O-benzyl-phosphino, phosphono, O-methyl-phosphono, O-ethyl-phosphono, O-n-propyl-phosphono, O-isopropyl-phosphono, O-benzyl-phosphono, O,O-dimethyl-phosphono, O,O-di-ethyl-phosphono, O,O-di-(n-propyl)phosphono, O,O-di-(isopropyl)phosphono, phosphonomethyl, O-methylphosphonomethyl, O-ethyl-phosphonomethyl, O-n-propylphosphonomethyl, O-isopropyl-phosphonomethyl, O-benzylphosphonomethyl, O,O-dimethyl-phosphonomethyl, O,O-diethyl-phosphonomethyl, O,O-di-(n-propyl)phosphonomethyl, O,O-di-(isopropyl)phosphonomethyl, phosphato, O-methyl-phosphato, O-ethyl-phosphato, O-n-propyl-phosphato, O-isopropyl-phosphato, O-benzylphosphato, O-phenyl-phosphato, O,O-dimethyl-phosphoryl, O,O-diethyl-phosphoryl, O,O-di-(n-propyl)phosphoryl or O,O-di-(isopropyl)-phosphoryl group, $R_1$ and $R_2$ may each denote a methyl, ethyl, n-propyl, isopropyl, n-butyl, isobutyl, tert.butyl, n-pentyl, isopentyl, neopentyl, n-hexyl, isohexyl, cyclopropyl, cyclobutyl, cyclopentyl, cyclohexyl, cycloheptyl, cyclopropylmethyl, 2-cyclopropylethyl, 3-cyclopropyl-n-propyl, 4-cyclopropyl-n-butyl, cyclobutylmethyl, 2-cyclobutylethyl, 3-cyclobutyl-n-propyl, 4-cyclobutyl-n-butyl, cyclopentylmethyl, 2-cyclopentylethyl, 3-cyclopentyl-n-propyl, 4-cyclopentyl-n-butyl, cyclohexylmethyl, 2-cyclohexyl-ethyl, 3-cyclohexyl-n-propyl, 4-cyclohexyl-n-butyl-, cycloheptylmethyl, 2-cycloheptylethyl, 3-cycloheptyl-n-propyl, 4-cycloheptyl-n-butyl, phenyl, phenylmethyl, 1-phenylethyl, 2-phenylethyl, 1-phenyl-n-propyl, 2-phenyl-n-propyl or 3-phenyl-n-propyl group, $R_1$ and $R_2$ together may denote an n-butylene, n-pentylene or n-hexylene group, $R_3$ may denote a hydrogen atom, or a methyl, ethyl, n-propyl, isopropyl, n-butyl, isobutyl or tert.-butyl group, $R_4$ may denote a hydrogen atom, a carboxymethoxy, 2-carboxy-ethoxy, 3-carboxy-propoxy, 4-carboxybutoxy, methoxycarbonylmethoxy, 2-methoxycarbonyl-ethoxy, 3-methoxycarbonyl-propoxy, 4-methoxycarbonyl-butoxy, ethoxycarbonylmethoxy, 2-ethoxycarbonyl-ethoxy, 3-ethoxycarbonyl-propoxy, 4-ethoxycarbonyl-butoxy, isopropyloxycarbonylmethoxy, 2-n-butoxycarbonyl-ethoxy, 3-isobutoxycarbonyl-propoxy, 4-tert.butoxycarbonylbutoxy, aminocarbonylmethoxy, 2-aminocarbonyl-ethoxy, 3-aminocarbonyl-propoxy, 4-aminocarbonyl-butoxy, methylaminocarbonylmethoxy, 2-methylaminocarbonyl-ethoxy, 3-methylaminocarbonyl-propoxy, 4-methylaminocarbonylbutoxy, ethylaminocarbonyl-methoxy, 2-ethylaminocarbonylethoxy, 3-ethylaminocarbonyl-propoxy, 4-ethylaminocarbonyl-butoxy, n-propylaminocarbonylmethoxy, 2-n-propylaminocarbonyl-ethoxy, 3-n-propylaminocarbonylpropoxy, 4-n-propylaminocarbonyl-butoxy, isopropylaminocarbonyl-methoxy, 2-n-butylaminocarbonylethoxy, 3-isobutylaminocarbonyl-propoxy, 4-isopropylaminocarbonyl-butoxy, dimethylaminocarbonylmethoxy, 2-dimethylaminocarbonylethoxy, 3-dimethylaminocarbonyl-propoxy, 4-dimethylaminocarbonyl-butoxy, diethylaminocarbonylmethoxy, 2-diethylaminocarbonylethoxy, 3-diethylaminocarbonyl-propoxy, 4-diethylaminocarbonyl-butoxy, di-n-propylaminocarbonyl-methoxy, 2-di-n-propylaminocarbonylethoxy, 3-di-n-propylaminocarbonyl-propoxy, O,O-dimethylphosphono-methoxy, O,O-diethylphosphono-methoxy, 4-di-n-propylaminocarbonyl-butoxy, diisopropylaminocarbonylmethoxy, 2-di-n-butylaminocarbonyl-ethoxy, 3-diisobutylaminocarbonyl-propoxy, 4-di-n-butylaminocarbonyl-butoxy, azido, 2-(imidazol-1-yl)-ethoxy, 3-(imidazol-1-yl)-propoxy, 4-(imidazol-1-yl)-butoxy, 2-(benzimidazol-1-yl)-ethoxy, 3-(benzimidazol-1-yl)-propoxy, 4-(benzimidazol-1-yl)-butoxy, quinolin-2-yl-methoxy, 2-(quinolin-2-yl)-ethoxy, 3-(quinolin-2-yl)-propoxy, 4-(quinolin-2-yl)-butoxy, isoquinolin-1-yl-methoxy, 2-(isoquinolin-1-yl)-ethoxy, 3-(isoquinolin-1-yl)-propoxy, 4-(isoquinolin-1-yl)-butoxy, isoquinolin-3-yl-methoxy, 2-(isoquinolin-3-yl)-ethoxy, 3-(isoquinolin-3-yl)-propoxy, 4-(isoquinolin-3-yl)-butoxy, pyridin-2-yl-methoxy, 2-(pyridin-2-yl)-ethoxy, 3-(pyridin-2-yl)-propoxy, 4-(pyridin-2-yl)-butoxy, pyridin-3-yl-methoxy, 2-(pyridin-3-yl)-ethoxy, 3-(pyridin-3-yl)-propoxy, 4-(pyridin-3-yl)-butoxy, pyridin-4-yl-methoxy, 2-(pyridin-4-yl)-ethoxy, 3-(pyridin-4-yl)-propoxy, 4-(pyridin-4-yl)butoxy, 4-methylimidazol-2-yl-methoxy, 2-(1-methylimidazol-4-yl)-ethoxy, 2-(1-methylimidazol-5-yl)-ethoxy, 2-(1-n-hexylimidazol-4-yl)-ethoxy, 2-(1-n-hexylimidazol-5-yl)-ethoxy, 1-benzylimidazol-4-yl-methoxy, 2-(1-benzylimidazol-5-yl)-ethoxy, 2-(1,2-dimethyl-imidazol-4-yl)-ethoxy, 2-(1,2-dimethylimidazol-5-yl)-ethoxy, 2-(2-methyl-imidazol-1-yl)-ethoxy, 2-(2-n-butyl-4-methyl-imidazol-1-yl)-ethoxy, 2-(2-n-butyl-5-methyl-imidazol-1-yl)-ethoxy, 2-(1-benzyl-2-methylimidazol-4-yl)-ethoxy, 2-(1-benzyl-2-methyl-imidazol-5-yl)-ethoxy, 2-(4,5-trimethylene-imidazol-2-yl)-ethoxy, 2-(4,5-trimethylene-imidazol-1-yl)-ethoxy, 2-(4,5-trimethylene-2-methyl-imidazol-1-yl)-ethoxy, 2-(benzimidazol-2-yl)-ethoxy, 2-(1-methylbenzimidazol-2-yl)-ethoxy, 2-(1-ethylbenzimidazol-2-yl)-ethoxy, 2-(1-n-propyl-benzimidazol-2-yl)-ethoxy, 2-(1-isopropylbenzimidazol-2-yl)-ethoxy, 2-(1-n-butylbenzimidazol-2-yl)-ethoxy, 2-(1-isobutylbenzimidazol-2-yl)-ethoxy, 2-(1-n-pentylbenzimidazol-2-yl)-ethoxy, 2-(1-n-hexylbenzimidazol-2-yl)-ethoxy, 2-(5-nitro-benzimidazol-1-yl)-ethoxy, 2-(5-amino-benzimidazol-2-yl)-ethoxy, 2-(5-acetamido-benzimidazol-2-yl)-ethoxy, 2-(5-methylbenzimidazol-2-yl)-ethoxy, 2-(5-methoxy-benzimidazol-2-yl)-ethoxy , 2-(5-ethoxy-benzimidazol-2-yl)-ethoxy, 2-(5-methyl-benzimidazol-1-yl)-ethoxy, 2-(6-methyl-benzimidazol-1-yl)-ethoxy, 2-(4-methyl-benzimidazol-1-yl)-ethoxy, 2-(5-chloro-benzimidazol-2-yl)-ethoxy, 2-(5-chloro-benzimidazol-1-yl)-ethoxy, 2-(6-chloro-1-methyl-benzimidazol-2-yl)-ethoxy, 2-(5,6-dimethoxy-1-methyl-benzimidazol-2-yl)-ethoxy, 2-(5,6-dimethoxy-benzimidazol-1-yl)-ethoxy, 2-(5-fluoro-1-methyl-benzimidazol-2-yl)-ethoxy, 2-(6-fluoro-benzimidazol-1-yl)-ethoxy, 2-(5-trifluoromethyl-benzimidazol-2-yl)-ethoxy, 2-(5-trifluoromethyl-benzimidazol-1-yl)-ethoxy, 2-(5-carboxy-1-methyl-benzimidazol-2-yl)-ethoxy, 2-(5 -aminocarbonyl-benzimidazol-2-yl)-ethoxy, 2-(5-aminocarbonyl-benzimidazol-1-yl)-ethoxy, 2-(5-methoxycarbonyl-1-methyl-benzimidazol-2-yl) -ethoxy, 2-(5-methylaminocarbonyl-1-methyl-benzimidazol-2-yl)-ethoxy, 2-(5-methylaminocarbonyl-benzimidazol-1-yl)-ethoxy, 2-(4,5,6,7-tetrahydro-benzimidazol-1-yl)-ethoxy, 2-(4,5,6,7-tetrahydro-1-methyl-benzimidazol-2-yl)-ethoxy, 2-(4,5,6,7-tetrahydro-1-ethyl-benzimidazol-2-yl)-ethoxy, 2-(4,5,6,7-tetrahydro-1-n-butyl-benzimidazol-2-yl)-ethoxy, 2-(4,5,6,7-tetrahydro-1-n-hexyl-benzimidazol-2-y 1)-ethoxy, (imidazo[1,2-a]pyridin-2-yl)-methoxy, (5-methyl-imidazo[1,2-a]pyridin-2-yl)-methoxy, (6-methyl-imidazo-[1,2-a]pyridin-2-yl)-methoxy, (7-methyl-imidazo[1,2-a]pyridin-2-yl)-methoxy, (8-methyl-imidazo[1,2-a]pyridin-2-yl)-methoxy, (5,7-dimethyl-imidazo[1,2-a]pyridin-2-yl)-methoxy, (6-aminocarbonyl-imidazo[1,2-a]pyridin-2-yl)-methoxy, (6-chloro-imidazo[1,2-a]pyridin-2-yl)-methoxy, (6-bromo-imidazo[1,2-a]pyridin-2-yl)-methoxy, (5,6,7,8-tetrahydro-imidazo[1,2-a]pyrimidin-2-yl)-methoxy, (imidazo[1,2-a]pyrimidin-2-yl)-methoxy, (5,7-dimethyl-imidazo[1,2-a]pyridin-2-yl)-methoxy, 2-(imidazo[4,5-b]pyridin-2-yl)-ethoxy, 2-(1-methyl-imidazo[4,5-b]pyridin-2-yl)-ethoxy, 2-(imidazo-[4,5-b]pyridin-1-yl)-ethoxy, 2-(4-methyl-imidazo[4,5-b]pyridin-2-yl)-ethoxy, 2-(6-methyl-imidazo[4,5-b]pyridin-2-yl)-ethoxy, 2-(4-methyl-imidazo[4,5-b]pyridin-1-yl)-ethoxy, 2-(6-methyl-imidazo[4,5-b]pyridin-1-yl)-ethoxy, 2-(imidazo-[4,5-c]pyridin-1-yl)-ethoxy, 2-(1-methyl-imidazo[4,5-c]pyridin-2-yl)-ethoxy, 2-(1-n-hexyl-imidazo[4,5-c]pyridin-2-yl)-ethoxy, 2-(imidazo[2,1-b]thiazol-6-yl)-ethoxy, 2-(3-methyl-imidazo[2,1-b]thiazol-6-yl)-ethoxy, 2-(2-phenyl-imidazo[2,1-b]thiazol-6-yl)-ethoxy, 2-(3-phenyl-imidazo[2,1-b]thiazol-6-yl)-ethoxy, 2-(2,3-dimethyl-imidazo[2,1-b]thiazol-6-yl)-ethoxy, 2 -(imidazo[1,2-c]pyrimidin-2-yl)-ethoxy, 2-(imidazo[1,2-a]pyrazin-2-yl)-ethoxy, 2-(imidazo[1,2-b]-pyridazin-2-yl)-ethoxy, 2-(imidazo[4,5-c]pyridin-2-yl)-ethoxy, 2-(purin-8-yl)-ethoxy or 2-(purin-9-yl)-ethoxy group, $R_5$ denotes a hydrogen atom and also the definitions given for $R_1$, $R_6$ denotes a hydrogen atom as well as the definitions given for $R_1$, $R_7$ denotes a hydrogen atom, a methyl, ethyl, n-propyl, isopropyl, n-butyl or isobutyl group, the $R_1CONR_7$ group may denote a pyrrolidin-2-one, piperidin-2-one or hexamethyleneimin-2-one group and the $R_1SO_2NR_7$ group may denote the propanesultam, butanesultam or pentanesultam group.

Preferred compounds of general formula I are those wherein $R_a$ denotes a straight-chained or branched $C_{1-4}$-alkyl group, a cyclopropyl, cyclobutyl, alkoxy, methoxymethyl or ethoxymethyl group, $R_b$ denotes a hydrogen, chlorine or bromine atom, an alkyl, aminomethyl, $R_1NHCH_2$ or $R_1NR_2CH_2$ group, wherein $R_1$ and $R_2$, Which may be identical or different, denote $C_{1-4}$-alkyl groups, cyclohexyl, phenyl or benzyl groups or $R_1$ and $R_2$ together denote an n-butylene group, $R_c$ denotes a hydrogen, chlorine or bromine atom, an alkyl or trifluoromethyl qroup, $R_d$ denotes a hydrogen atom or an alkyl group, $R_e$ denotes a carboxy or a 1H-tetrazol-5-yl group, X denotes an oxygen atom, an imino group optionally substituted by a formyl, $R_1$ or $R_1CO$ group, or a —CO—, —(HON=C)— or —($R_3CR_4$)— group, wherein $R_3$ denotes a hydrogen atom or an alkyl group and $R_4$ denotes a hydrogen atom, an alkoxy group substituted by a carboxy, alkoxycarbonyl, aminocarbonyl, alkylaminocarbonyl, dialkylaminocarbonyl or heteroaryl group, wherein the heteroaryl group is linked to the alkoxy group via a carbon-carbon bond, an alkoxy group substituted in the 2, 3 or 4-position by a heteroaryl group, in which the heteroaryl group is linked to the alkoxy group via a carbon-nitrogen bond, a hydroxy, $R_1O$—, $R_1CO$—O—, $R_1O$—CO—O, azido, $R_5NR_6$—, CHO—$NR_5$—, $R_1$—CO—$NR_7$—, $R_1O$—CO—$NR_5$—, $R_5NR_6$—CO—O—, —$R_1$-$SO_2$—O—, $R_5NR_6$—CO—$NR_5$— or $R_1SO_2$—$NR_7$— group, whilst in the above-mentioned groups, $R_1$ is as hereinbefore defined, $R_5$ and $R_6$, which may be identical or different, denote hydrogen atoms or have the meanings given for $R_1$ hereinbefore, $R_7$ denotes a hydrogen atom or an alkyl group or $R_1$ and $R_7$ together denote a $C_{3-5}$-n-alkylene group, whilst unless otherwise specified an alkyl or alkoxy moiety mentioned above may contain 1 to 3 carbon atoms and a cycloalkyl moiety mentioned above may contain 3 to 7 carbon atoms, the enantiomers and the salts thereof, particularly, for pharmaceutical use, the physiologically acceptable salts thereof with inorganic or organic acids or bases.

Particularly preferred compounds of general formula I above are those wherein $R_a$ denotes a $C_{2-4}$-alkyl group, $R_b$ denotes a hydrogen atom, $R_c$ denotes a hydrogen atom or a methyl group, $R_d$ denotes a hydrogen atom, $R_e$ denotes a carboxy or 1H-tetrazolyl group and X denotes a carbonyl group or a methylene group optionally substituted by a hydroxy, methoxy, benzyloxy, pyridylmethoxy, acetoxy, ethoxycarbonylmethoxy, cyclohexylcarbonyloxy or cyclohexylaminocarbonyloxy group, the enantiomers and the salts thereof, particularly for pharmaceutical use the physiologically acceptable salts thereof with inorganic or organic acids or bases.

According to the invention, the compounds are obtained by the following methods:

a) In order to prepare a compound of general formula I wherein X denotes an —(HOCR_3)— group and $R_b$ denotes a hydrogen, fluorine or chlorine atom or an alkyl or trifluoromethyl group:

Reacting an imidazo[1,2-a]pyridine of general formula

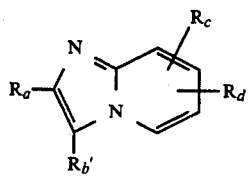

(II)

wherein $R_a$, $R_c$ and $R_d$ are as hereinbefore defined and $R_b$ denotes a hydrogen, fluorine or chlorine atom or an alkyl or trifluoromethyl group, with a biphenyl compound of general formula

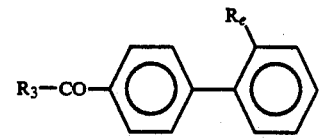

(III)

wherein $R_e$ and $R_3$ are as hereinbefore defined.

The reaction is carried out under the action of a strong base such as potassium tert.butoxide, sodium hydride, lithium amide, sodium amide, lithium diisopropylamide, lithium-2,2,6,6-tetramethylpiperidide, lithium hexamethyldisilazide or an organolithium compound such as methyllithium, ethyllithium, n-butyllithium, sec.butyllithium, tert.butyllithium, phenyllithium or optionally an equimolar mixture of n-butyllithium with potassium tert.butoxide, n-butyllithium with N,N,N',N'-tetramethyleneethylenediamine or n-butyllithium with N,N,N',N'-tetramethyleneethylenediamine and potassium tert.butoxide (see for example "Lambert Brandsma, Hermann Verkruisse, Preparative Polar Organometallic Chemistry I, Springer Verlag 1987") on a compound of general formula II, conveniently in a solvent or mixture of solvents such as diethylether, tetrahydrofuran, dioxane or liquid ammonia, at temperatures between −100° C. and 20° C., preferably at temperatures between −78° C. and −20° C., and subsequent reaction with a compound of general formula III at −100° C. to −50° C., preferably at −78° C., and subsequent heating to 20° C. to 50° C., preferably to ambient temperature.

b) In order to prepare a compound of general formula I wherein $R_e$ denotes a carboxy group:

Converting a compound of general formula

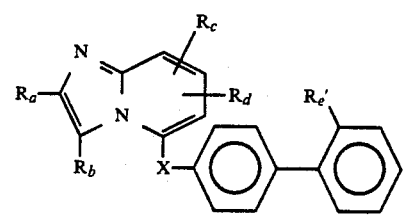

(IV)

wherein $R_a$ to $R_d$ and X are as hereinbefore defined and $R_e'$ denotes a group which may be converted into a carboxy group by hydrolysis, thermolysis or hydrogenolysis, into a corresponding carboxyl compound.

For example, functicnal derivatives of the carboxy group such as unsubstituted or substituted amides, esters, thiolesters, orthoesters, iminoethers, amidines or anhydrides, a nitrile group or a tetrazolyl group may be converted into a carboxy group by hydrolysis, esters with tertiary alcohols, e.g. tert.butylester, may be converted into a carboxy group by thermolysis and esters with aralkanols, e.g. benzylester, may be converted into a carboxy group by hydrogenolysis.

The hydrolysis is conveniently carried out in the presence of an acid such as hydrochloric acid, sulphuric acid, phosphoric acid, trichloroacetic acid or trifluoroacetic acid or in the presence of a base such as sodium hydroxide or potassium hydroxide in a suitable solvent such as water, water/methanol, ethanol, water/ethanol, water/isopropanol or water/dioxane, at temperatures between −10° C. and 120° C., e.g. at temperatures between ambient temperature and the boiling temperature of the reaction mixture. When hydrolysis is carried out in the presence of an organic acid such as trichloroacetic or trifluoroacetic acid, any alcoholic hydroxy groups present may optionally be simultaneously converted into a corresponding acyloxy group such as a trifluoroacetoxy group.

If $R_e'$ in a compound of general formula IV represents a cyano or aminocarbonyl group, these groups may also be converted into a carboxy group with a nitrite, e.g. sodium nitrite, in the presence of an acid such as sulphuric acid, which may also be simultaneously used as solvent, at temperatures between 0° C. and 50° C.

If $R_e'$ in a compound of general formula IV represents, for example, a tert.-butyloxycarbonyl group, the tert.-butyl group may also be thermally cleaved, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C.

If $R_e'$ in a compound of general formula IV represents, for example, a benzyloxycarbonyl group, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° C. and 50° C., e.g. at ambient temperature, and under a hydrogen pressure of 1 to 5 bar. During hydrogenolysis, other groups may be reduced at the same time, e.g. a nitro group may be reduced to an amino group, a benzyloxy group to a hydroxy group, a vinylidene group to the corresponding alkylidene group or a cinnamic acid group to the corresponding phenylpropionic acid group, or they may be replaced by hydrogen atoms, e.g. a halogen may be replaced by a hydrogen atom.

c) In order to prepare a compound of general formula I wherein X denotes a carbonyl group:
Oxidation of a compound of general formula

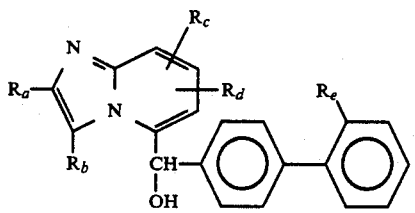

(V)

wherein
$R_a$ to $R_e$ are as hereinbefore defined.

The oxidation is preferably carried out in a solvent or mixture of solvents, e.g. in acetone, pyridine, water/pyridine, glacial acetic acid, dichloromethane or chloroform at temperatures between −20° C. and 100° C. The oxidizing agent used may be, for example, chromic acid in glacial acetic acid or in acetone or modified chromic acid reagents such as pyridinium chlorochromate or pyridinium dichromate in dichloromethane, manganese dioxide in chloroform, potassium permanganate in glacial acetic acid, pyridine or in acetone, sodium hypochlorite in glacial acetic acid, dimethylsulphoxide combined with acetic anhydride, trifluoroacetic anhydride, dicyclohexylcarbodiimide or combined with oxalylchloride and triethylamine, preferably at temperatures between 0° C. and 20° C.

d) In order to prepare a compound of general formula I wherein X denotes an ($R_3$CH) group:
Reduction of a compound of general formula

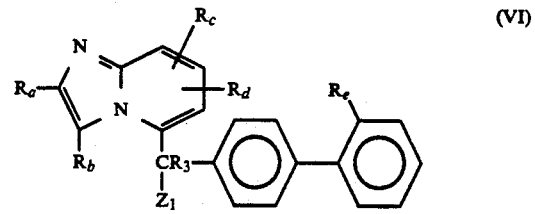

(VI)

wherein
$R_a$ to $R_e$ and $R_3$ are as hereinbefore defined and
$Z_1$ denotes a group which can be replaced by a hydride, e.g. a chlorine, bromine or iodine atom, a hydroxy, p-toluenesulphonyloxy, $R_8$—CO— or $R_8$—CS— group, wherein $R_5$ denotes a phenyl, phenyloxy, phenylthio or $C_{1-3}$-alkoxy group, with an organometallic hydride.

The reaction is conveniently carried out in a solvent or mixture of solvents such as benzene or toluene, using an organometallic hydride such as tri-n-butyl tin hydride or tri-n-propylsilane at temperatures between 50° C. and 150° C., preferably at the boiling temperature of the reaction mixture.

e) In order to prepare a compound of general formula I wherein X denotes an —$R_1$N— or —($R_3$CR$_4$)— group in which $R_1$ is as hereinbefore defined with the exception of the cyclopropyl, cyclobutyl and phenyl groups, and $R_3$ is as hereinbefore defined and $R_4$ denotes a $C_{1-4}$-alkoxy group substituted by a carboxy, alkoxycarbonyl, aminocarbonyl, alkylaminocarbonyl, dialkylaminocarbonyl or heteroaryl group, wherein the heteroaryl group is linked to the alkoxy group via a carbon-carbon bond, a $C_{2-4}$-alkoxy group substituted in the 2, 3 or 4-position by a heteroaryl group, wherein the heteroaryl group is linked to the alkoxy group via a carbon-nitrogen bond, or an $R_1$O or $R_1$NR$_6$ group wherein $R_1$ and $R_3$ are defined as above and $R_6$ is as hereinbefore defined:
Reacting a compound of general formula

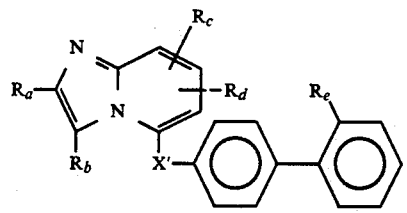

(VII)

wherein
$R_a$ to $R_e$ are as hereinbefore defined and
X' denotes an —HN— or —(HO—CR$_3$)— group in which $R_3$ is as hereinbefore defined, with a compound of formula $R_1'$—$Z_2$ (VIII)

wherein $R_1'$ has the meanings given for $R_1$ hereinbefore with the exception of the cyclopropyl, cyclobutyl and phenyl groups and additionally denotes a $C_{1-4}$-alkyl group substituted by a carboxy, alkoxycarbonyl, aminocarbonyl, alkylaminocarbonyl, dialkylaminocarbonyl or heteroaryl group, wherein the heteroaryl group is linked to the alkyl group via a carbon-carbon bond, or a $C_{2-4}$-alkyl group substituted in the 2, 3 or 4-position by a heteroaryl group, wherein the heteroaryl group is linked to the alkyl group via a carbon-nitrogen bond, and $Z_2$ denotes a nucleophilic leaving group such as a halogen atom, e.g. a chlorine, bromine or iodine atom, or a substituted sulphonyloxy group, e.g. a methanesulphonyloxy, phenylsulphonyloxy or p-toluenesulphonyloxy group.

The reaction is conveniently carried out in a solvent or mixture of solvents such as methylene chloride, diethylether, tetrahydrofuran, dioxane, dimethylsulphoxide, dimethylformamide or benzene, optionally in the presence of an acid binding agent such as sodium carbonate, potassium carbonate, sodium hydroxide, sodium hydride, potassium tert.-butoxide, triethylamine or pyridine, whilst the latter two may simultaneously also be used as solvent, preferably at temperatures between 0° C. and 100° C., e.g. at temperatures between ambient temperature and 50° C.

f) In order to prepare a compound of general formula I wherein X denotes an —($R_1$—CO—N)—, —($R_1$—CO—O—$CR_3$)—, —($R_1$O—CO—O—$CR_3$)—, —($R_1$—$SO_2$—O—$CR_3$)—, —($R_1$—CO—$NR_7$—$CR_3$)—, —($R_1$O—$CONR_5$—$CR_3$)— or —($R_1SO_2$—$NR_7$—$CR_3$)— group:

Acylating a compound of formula

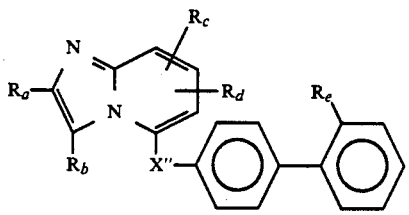
(IX)

wherein $X''$ denotes an —HN—, —(HO—$CR_3$)— or —($R_5$NH—$CR_3$)— group, wherein $R_3$ and $R_5$ are as hereinbefore defined, with a compound of formula

$Z_3$—U—E         (X)

wherein $Z_3$ denotes a nucleophilic leaving group,

U denotes a carbonyl or sulphonyl group and E has the meanings given for $R_1$ hereinbefore or E together with $R_5$ denotes a $C_{3-5}$-n-alkylene group or, if U denotes a carbonyl group, an $R_1O$ group in which $R_1$ is as hereinbefore defined, or with the reactive derivatives thereof such as the acid halides, acid esters or acid anhydrides thereof.

Examples of reactive derivatives of a compound of formula X include the esters thereof, such as the methyl, ethyl or benzylesters, the thioesters thereof such as the methylthio or ethylthioesters, the halides thereof such as the acid chloride, the anhydrides or imidazolides thereof and the orthoesters thereof.

The reaction is expediently carried out in a solvent or mixture of solvents such as water, methylene chloride, chloroform, ether, tetrahydrofuran, dioxane or dimethylformamide or in an excess of the acylating agent as solvent with a corresponding carboxylic acid in the presence of an acid activating or dehydrating agent such as thionylchloride, with the anhydrides thereof such as acetic acid anhydride, with the esters thereof such as ethyl acetate, with the halides thereof such as acetyl chloride or methanesulphonyl chloride, optionally in the presence of an inorganic or tertiary organic base, such as sodium hydroxide, potassium carbonate, triethylamine or pyridine, whilst the latter two may simultaneously also be used as solvent, at temperatures between −25° C. and 100° C., but preferably at temperatures between −10° C. and 80° C.

g) In order to prepare a compound of general formula I wherein X denotes an —($R_5NR_6$—CO—O—$CR_3$)— or —($R_5NR_6$—CO—$NR_5$—$CR_3$)— group:

Reacting a compound of general formula

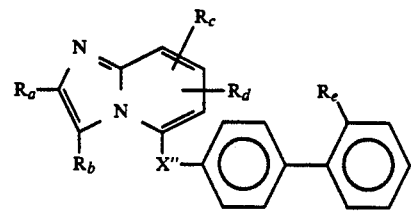
(IX)

wherein $R_a$ to $R_e$ and $R_3$ are as hereinbefore defined and $X''$ denotes an —(HO—$CR_3$)— or —($R_5$NH—$CR_3$)— group, wherein $R_3$ and $R_5$ are as hereinbefore defined, with a compound of general formula

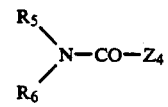
(XI)

optionally formed in the reaction mixture, wherein $R_5$ and $R_6$ are as hereinbefore defined and $Z_4$ denotes a nucleophilic leaving group such as a chlorine or bromine atom or $Z_4$ and $R_5$ together denote a nitrogen-carbon bond.

The reaction is conveniently carried out in a solvent or mixture of solvents such as dichloromethane, chloroform, diethylether, tetrahydrofuran, dioxane, dimethylformamide, dimethylsulphoxide, pyridine, benzene or toluene at temperatures between 0° C. and 150° C., but preferably at temperatures between 50° C. and 120° C.

h) In order to prepare a compound of general formula I wherein $R_e$ denotes a 1H-tetrazolyl group:

Cleaving a protective group from a compound of general formula

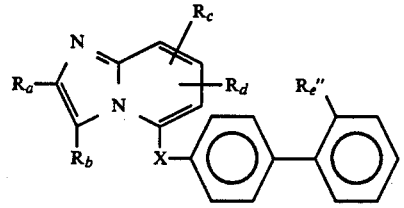
(XII)

wherein $R_a$ to $R_d$ and X are as hereinbefore defined and
$R_e''$ denotes a 1H-tetrazolyl group protected in the 1— or 2-position by a protecting group.

Suitable protecting groups include, for example, the β-cyanoethyl, triphenylmethyl, tributyl tin or triphenyl tin groups.

The cleaving of a protective group used is preferably carried out in the presence of a hydrohalic acid, preferably in the presence of hydrochloric acid, in the presence of a base such as sodium hydroxide or alcoholic ammonia, in a suitable solvent such as methylene chloride, methanol, methanol/ammonia, ethanol or isopropanol, at temperatures between 0° C. and 100° C., but preferably at ambient temperature or, if the reaction is carried out in the presence of alcoholic ammonia, at elevated temperatures, e.g. at temperatures between 100° C. and 150° C., preferably at temperatures between 120° C. and 140° C.

i) In order to prepare a compound of general formula I wherein X denotes an oxygen atom or an $R_5N$ group:

Reacting an imidazo[1,2-a]pyridine of general formula

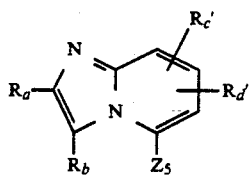

wherein
$R_a$ and $R_b$ are as hereinbefore defined, '$R_c'$' denotes a hydrogen atom or an alkyl group,
$R_d'$ denotes a hydrogen atom and
$Z_5$ denotes a nucleophilic leaving group such as a chlorine or bromine atom, with a biphenyl compound of general formula

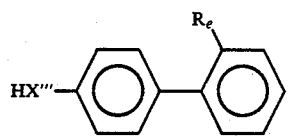

wherein
$R_e$ is as hereinbefore defined and
$X'''$ denotes an oxygen atom or an $R_5N$ group wherein $R_5$ is as hereinbefore defined.

The reaction is expediently carried out in a solvent or mixture of solvents such as methylene chloride, diethylether, tetrahydrofuran, dioxane, dimethylsulphoxide, dimethylformamide or benzene, optionally in the presence of an acid binding agent such as sodium carbonate, potassium carbonate, sodium hydroxide, sodium hydride, potassium tert.butoxide, triethylamine or pyridine, whilst the latter two may simultaneously also be used as solvent, preferably at temperatures between 0° C. and 100° C., e.g. at temperatures between ambient temperature and 50° C.

j) In order to prepare a compound of general formula I wherein $R_e$ denotes a 1H-tetrazolyl group:

Reacting a compound of general formula

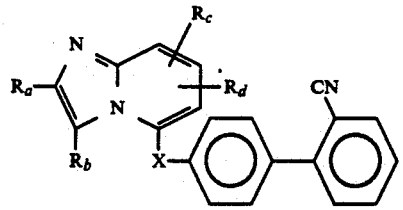

wherein
$R_a$ to $R_d$ and X are as hereinbefore defined, with hydrazoic acid or the salts thereof.

The reaction is preferably carried out in a solvent such as benzene, toluene or dimethylformamide at temperatures between 80° C. and 150° C., preferably at 125° C.

Conveniently, either the hydrazoic acid is liberated during the reaction from an alkali metal azide, e.g. from sodium azide, in the presence of a weak acid such as ammonium chloride, or a tetrazolide salt obtained in the reaction mixture during the reaction with a salt of hydrazoic acid, preferably with aluminium azide or tributyl tin azide, which is also preferably produced in the reaction mixture by reacting aluminium chloride or tributyl tin chloride with an alkali metal azide such as sodium azide, is subsequently liberated by acidification with a dilute acid such as 2N hydrochloric acid or 2N sulphuric acid.

If according to the invention a compound of formula I is obtained wherein $R_b$ denotes a hydrogen atom it may be converted by nitration into a corresponding compound of formula I wherein $R_b$ denotes a nitro group, or if a compound of formula I is obtained wherein $R_b$ denotes a nitro group, this may be converted after reduction into a corresponding amino compound of formula I via the corresponding diazonium salts into a compound of formula I wherein $R_b$ denotes a hydrogen, fluorine, chlorine or bromine atom, or if a compound of formula I is obtained wherein $R_b$ denotes a hydrogen atom, this may be converted by halogenation into a corresponding compound of formula I wherein $R_b$ denotes a chlorine or bromine atom, or if a compound of formula I is obtained wherein $R_b$ denotes a hydrogen atom, this may be converted by reaction with disubstituted formamides, e.g. with dimethylformamide or n-methylformanilide and phosphorusoxychloride, in accordance with a Vilsmeier-Haack reaction, into a compound of formula I wherein $R_b$ denotes a formyl group, or if a compound of formula I is obtained wherein $R_b$ denotes a formyl group, this may be converted by oxidation into a compound of formula I wherein $R_b$ denotes a carboxy group, or if a compound of formula I is obtained wherein $R_b$ denotes a carboxy group, this may be converted by esterification into a compound of formula I wherein $R_b$ denotes an alkoxycarbonyl group, or if a compound of formula I is obtained wherein $R_b$ denotes a formyl group, this may be converted by reaction with hydroxylamine into a corresponding aldoxime of formula I and by subsequent reaction of the aldoxime with a dehydrating agent into a compound of formula I wherein $R_b$ denotes a cyano group, or if a compound of formula I is obtained wherein $R_b$ denotes a hydrogen atom, this may be converted by reaction with ammonia or a primary or secondary amine and formaldehyde by a Mannich reaction into a compound of formula I wherein $R_b$ denotes an $NH_2CH_2-$, $R_1NHCH_2-$ or $R_1NR_2CH_2-$ group, wherein $R_1$ and $R_2$ are as hereinbefore defined, or if a compound of formula I is obtained wherein X denotes an $-(R_1SO_2O-CR_3)-$ group, this may be converted by reaction with sodium azide into the corresponding azido compound of formula I and optionally by subsequent reduction into the corresponding amino compound of formula I or if a compound of formula I is obtained wherein X denotes a carbonyl group, this may be converted by reaction with hydroxylamine into the corresponding compound of formula I wherein X denotes an $-(HON=C)-$ group, and optionally by subsequent reduction into the corresponding amino compound of formula I or if a compound of formula I is obtained wherein X denotes a carbonyl group, this may be converted by reaction with 1,2-ethanediol or 1,3-propanediol into the corresponding compound of formula I wherein X denotes an $-(R_3CR_4)$-group, wherein $R_3$ and $R_4$ together denote a 1,2-ethylenedioxy or 1,3-n-propylenedioxy group.

The subsequent nitration is carried out using concentrated to semiconcentrated nitric acid in water, glacial acetic acid or acetic anhydride, using a mixture of concentrated nitric acid and concentrated sulphuric acid, with dinitrogen pentoxide in carbon tetrachloride and in the presence of phosphorus pentoxide, with ethyl nitrate, optionally in the presence of a Lewis or Brönsted acid, with sodium nitrite in the presence of trifluoroacetic acid or using a nitronium salt, e.g. nitronium tetrafluoroborate or nitronium trifluoromethanesulphonate, at temperatures between 0° C. and 100° C., preferably at temperatures between 20° C. and 50° C.

The subsequent reduction of the nitro group is preferably carried out in a solvent such as water, water/ethanol, methanol, glacial acetic acid, ethyl acetate or dimethylformamide, expediently with hydrogen in the presence of a hydrogenation catalyst such as Raney nickel, platinum or palladium/charcoal, with metals such as iron, tin or zinc in the presence of an acid, with salts such as iron(II)sulphate, tin(II)chloride, sodium sulphide, sodium hydrogen sulphite or sodium dithionite, or with hydrazine in the presence of Raney nickel, at temperatures between 0° C. and 80° C., preferably at temperatures between 20° C. and 40° C.

The subsequent reaction of a diazonium salt, e.g. the tetrafluoroborate, the hydrosulphate in sulphuric acid, the hydrochloride or the hydroiodide, if necessary in the presence of copper or a corresponding copper-(I)-salt such as copper-(I)-chloride/hydrochloric acid or copper-(I)-bromide/hydrobromic acid, is carried out at slightly elevated temperatures, e.g. at temperatures between 15° C. and 100° C., whilst the subsequent reaction of a tetrafluoroborate may also be carried out by heating the previously isolated and dried diazonium salt or by heating the diazonium salt in an inert solvent, e.g. in dichloromethane, n-hexane, benzene or toluene. The subsequent reaction with hypophosphoric acid is preferably carried out at −5° C. to 0° C. The diazonium salt required for this is conveniently prepared in a suitable solvent, e.g. in water/hydrochloric acid, methanol/hydrochloric acid, ethanol/hydrochloric acid or dioxane/hydrochloric acid, by diazotising a corresponding amino compound with a nitrite, e.g. sodium nitrite or an ester of nitric acid, at low temperatures, e.g. at temperatures between −10° C. and 5° C.

The subsequent halogenation is carried out under the action of elemental chlorine or bromine, optionally with the addition of iron powder or a suitable Lewis acid, e.g. iron-III-chloride, iron-III-bromide, aluminium trichloride, zinc chloride or copper-II-chloride, preferably in an inert solvent such as chloroform or carbon tetrachloride, at temperatures between 0° C. and 80° C., preferably at temperatures between 20° C. and 50° C.

The subsequent formylation is carried out by reacting with a Vilsmeier reagent which is preferably prepared in the reaction mixture by reacting dimethylformamide or N-methylformanilide and phosphorusoxychloride, whilst conveniently using the formamide as solvent at the same time, at temperatures between 0° C. and 80° C., preferably at temperatures between 20° C. and 50° C.

The subsequent oxidation is preferably carried out in a solvent or mixture of solvents, e.g. in acetone, pyridine, water/pyridine, glacial acetic acid, dichloromethane or chloroform at temperatures between −20° C. and 100° C. The oxidising agent used may be, for example, chromic acid in glacial acetic acid or in acetone, manganese dioxide in chloroform or potassium permanganate in glacial acetic acid, pyridine or in acetone.

The subsequent esterification is conveniently carried out in a suitable solvent, e.g. in a corresponding alcohol, pyridine, toluene, methylene chloride, tetrahydrofuran or dioxane, in the presence of an acid activating and/or dehydrating agent such as thionylchloride, ethylchloroformate, carbonyldiimidazole or N,N'-dicyclohexylcarbodiimide or the isourea ethers thereof, optionally in the presence of a reaction accelerator such as copper chloride, or by transesterification, e.g. with a corresponding carbonic acid diester, at temperatures between 0° C. and 100° C., but preferably at temperatures between 20° C. and the boiling temperature of the solvent in question.

The subsequent oxime formation is preferably carried out in a solvent such as methanol, ethanol, dichloromethane, tetrahydrofuran, dioxane, benzene or toluene by reacting with hydroxylamine, conveniently in the presence of a catalytic amount of an acid such as hydrochloric acid or sulphuric acid, at temperatures between 0° C. and 50° C., preferably at temperatures between 10° C. and 30° C.

The subsequent dehydration of a corresponding oxime compound is carried out with a dehydrating agent such as phosphorus pentoxide, sulphuric acid or p-toluenesulphonic acid chloride, optionally in a solvent such as methylene chloride or pyridine, at temperatures between 0° C. and 100° C., preferably at temperatures between 20° C. and 80° C.

The subsequent reaction with ammonia or a primary or secondary amine and formaldehyde in a Mannich reaction is expediently carried out in a suitable solvent or mixture of solvents such as water, methanol, ethanol, ethanol/water or dioxane, optionally with the addition of acetic acid, at a temperature of between 0° C. and 80° C., preferably at temperatures between 20° C. and 50° C.

The subsequent preparation of an azide is preferably carried out in a solvent such as water/methanol, water/acetone, ethanol, tetrahydrofuran or dioxane, by reacting a corresponding sulphonic acid ester with an alkali metal azide, such as sodium azide, at temperatures between 0° C. and 50° C., preferably at ambient temperature.

The subsequent dioxolane or dioxane formation is carried out in the presence of a corresponding 1,2 or 1,3-dihydroxyalkane, which is conveniently used as solvent at the same time, usefully in the presence of a catalytic amount of an acid such as sulphuric acid or p-toluenesulphonic acid, at temperatures of between 20° C. and 100° C., preferably between 30° C. and 80° C.

In the reactions described hereinbefore, any reactive groups present such as hydroxy, amino, alkylamino or formyl groups may be protected during the reaction by conventional protecting groups which are split off again after the reaction.

Examples of protecting groups for a hydroxy group are trimethylsilyl, acetyl, benzoyl, methyl, ethyl, tert-butyl, benzyl or tetrahydropyranyl groups and protecting groups for an amino, alkylamino or imino group are acetyl, benzoyl, ethoxycarbonyl, phthalyl or benzyl groups and protecting groups for a formyl group are acetal or thioacetal groups, e.g. the 1,2-ethylenedioxy, 1,3-n-propylenedioxy, 1,2-ethylenedithio or 1,3-n-propylenedithio groups.

The optional subsequent cleaving of a protecting group is preferably carried out by hydrolysis in an aqueous solvent, e.g. in water, isopropanol/water, tetrahydrofuran/water or dioxane/water, in the presence of an acid such as hydrochloric acid or sulphuric acid or in the presence of an alkali metal base such as sodium hydroxide or potassium hydroxide, at temperatures between 0° C. and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid, at temperatures between 0° C. and 50° C., but preferably at ambient temperature, under a hydrogen pressure of 1 to 7 bar, preferably 3 to 5 bar.

Furthermore, the compounds of general formula I obtained having at least one optically active carbon atom may be resolved into their enantiomers.

Thus, for example, the compounds of general formula I which occur in racemate form may be separated by methods known per se (cf. Allinger N.L. and Eliel E.L. in "Topics in Stereochemistry", Vol. 6, Wiley Interscience, 1971) into their optical antipodes and compounds of general formula I having at least 2 asymmetric carbon atoms may be separated on the basis of their physical-chemical differences using known methods, e.g. by chromatography and/or fractional crystallisation, into the diastereomers thereof which, if they occur in racemic form, may subsequently be separated into the enantiomers as mentioned above.

The separation of enantiomers is preferably effected by column separation on chiral phases or by recrystallisation from an optically active solvent or by reacting with an optically active substance which forms salts or derivatives such as esters or amides with the racemic compound, especially acids and the activated derivatives or alcohols thereof, and separation of the diastereomeric salt mixture or derivative thus obtained, e.g. on the basis of their different solubilities, whilst the free antipodes may be released from the pure diastereomeric salts or derivatives by the action of suitable agents. Particularly common, optically active acids include, for example, the D- and L-forms of tartaric acid or dibenzoyltartaric acid, di-o-tolyl tartaric acid, malic acid, mandelic acid, camphorsulphonic acid, glutamic acid, aspartic acid or quinic acid. The optically active alcohol may be (+)- or (−)-menthol, for example, and the optically active acyl group in amides may be, for example, (+)- or (−)-menthyloxycarbonyl.

Moreover, the compounds of general formula I obtained may be converted into the acid addition salts thereof, more particularly for pharmaceutical use the physiologically acceptable salts thereof with inorganic or organic acids. Suitable acids for this purpose include hydrochloric acid, hydrobromic acid, sulphuric acid, phosphoric acid, fumaric acid, succinic acid, lactic acid, citric acid, tartaric acid or maleic acid.

Furthermore, the new compounds of general formula I thus obtained, if they contain a carboxy or 1H-tetrazolyl group, may if desired subsequently be converted into the salts thereof with inorganic or organic bases, more particularly for pharmaceutical use into the physiologically acceptable addition salts thereof. Suitable bases include for example sodium hydroxide, potassium hydroxide, cyclohexylamine, ethanolamine, diethanolamine and triethanolamine.

The compounds of general formula II to XV used as starting materials are known from the literature in some cases or may be obtained by methods known from the literature.

Thus, for example, a compound of general formula II wherein $R_a$ denotes a straight-chained or branched $C_{1-6}$-alkyl group, a cycloalkyl group or an alkyl group substituted by an alkoxy group and $R_b'$ denotes a hydrogen atom or an alkyl group, or which is substituted in the 3-position by an alkoxycarbonyl group, is obtained by reacting a corresponding 2-aminopyridine of general formula

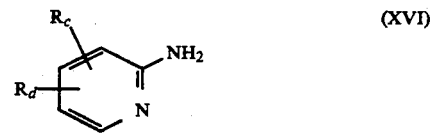

(XVI)

wherein $R_c$ and $R_d$ are as hereinbefore defined, with a carbonyl compound of the formula

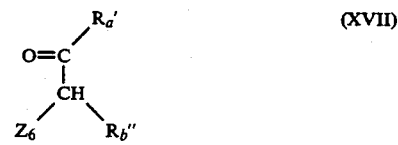

(XVII)

wherein $R_a'$ denotes a straight-chained or branched $C_{1-6}$-alkyl group, a cycloalkyl group or an alkoxy-substituted alkyl group, $R_b''$ denotes a hydrogen atom, an alkyl group or an alkoxycarbonyl group and $Z_6$ denotes a nucleophilic leaving group such as a halogen atom, e.g. a chlorine, bromine or iodine atom, or a substituted sulphonyloxy group, e.g. a methanesulphonyloxy, phenylsulphonyloxy or p-toluenesulphonyloxy group.

The reaction is conveniently carried out in a solvent or mixture of solvents such as ethanol, isopropanol, benzene, glycol, glycolmonomethylether, 1,2-dimethoxyethane, methylene chloride, diethylether, tetrahydrofuran, dioxane, dimethylsulphoxide or dimethylformamide, optionally in the presence of an acid binding agent, such as sodium carbonate, potassium carbonate, triethylamine or pyridine, whilst the latter two may also be used as solvent, e.g. at temperatures between 0° C. and 150° C., preferably at temperatures between 20° C. and 100° C. However, the reaction may also be carried out without a solvent.

A compound of formula II wherein $R_a$ denotes an alkoxy group and which is substituted in the 3-position by an alkoxycarbonyl group, is obtained, for example, analogously to the method described in EP-A-383319 by reacting a 2-aminopyridine of general formula XVI with chloroacetic acid, subsequent alkaline hydrolysis and chlorination with phosphorusoxychloride to obtain the corresponding 2-chloro-imidazo[1,2-a]pyridine derivative, introducing the ethoxycarbonyl group into the 3-position by metallising with n-butyllithium and reacting the aryllithium compound with ethylchloroformate and subsequently substituting the chlorine atom in the 2-position by an alkoxy group by reacting with a corresponding sodium alkoxide, optionally with simultaneous transesterification of the ethoxycarbonyl group into a corresponding alkoxycarbonyl group.

A compound of formula II wherein $R_a$ denotes an alkoxy group and $R_b'$ denotes a hydrogen atom is obtained by saponification and subsequent decarboxylation of a compound of formula II wherein $R_a$ denotes an alkoxy group and which is substituted in the 3-position by an alkoxycarbonyl group.

A compound of formula II wherein $R_b'$ denotes a trifluoromethyl group is obtained by reacting a compound of formula II, substituted in the 3-position by a carboxy or alkoxycarbonyl group, with a fluorinating agent, e.g. with diethylaminosulphur trifluoride, perchloryl fluoride or molybdenum hexafluoride.

A compound of formula II wherein $R_b'$ denotes a hydroxymethyl group is Obtained by reduction of a compound of formula II which is substituted in the 3-position by an alkoxycarbonyl group, e.g. with lithium aluminium hydride, lithium borohydride, diisobutylaluminium hydride, lithium triethylborohydride or triethoxysilane.

A compound of formula II wherein $R_a$ denotes an alkoxy group and $R_b'$ denotes an alkyl group is obtained by reduction of a corresponding carbonyl compound of formula II wherein $R_a$ denotes an alkoxy group.

The compounds of general formulae IV, V, VI, VII, IX, XII and XV used as starting materials are preferably obtained by reacting a corresponding imidazo[1,2-a]pyridine with a corresponding biphenylcarbonyl compound.

A hydroxymethylene compound thus obtained is later converted into the desired compound by acylation, alkylation, azide formation and subsequent reduction.

The compounds of general formula XIII used as starting materials are obtained by reacting a suitable substituted aminopyridine with a correspondingly substituted β-ketocarbonyl compound.

The new compounds of general formula I and the physiologically acceptable salts thereof have valuable pharmacological properties. They are angiotensin-antagonists, particularly angiotensin-II-antagonists.

For example, the following compounds:

A=(R,S)-2-ethyl-8-methyl-5-[α-(2'-carboxybiphenyl-4-yl)-α-hydroxy-methyl]imidazo[1,2-a]pyridine, B=(R,S)-2-ethyl-8-methyl-5-[α-(2'-carboxybiphenyl-4-yl)-α-acetoxy-methyl]imidazo[1,2-a]pyridine, C=(R,S)-2-ethyl-8-methyl-5-[α-(2'-carboxybiphenyl-4-yl)-α-cyclohexylaminocarbonyloxy-methyl]imidazo[1,2-a]pyridine and D=(R,S)-2-n-propyl-8-methyl-5-[α-(2'-carboxybiphenyl-4-yl)-α-hydroxy-methyl]imidazo[1,2-a]pyridine-hydrate were tested for their biological effects as follows:

Description of Method: Angiotensin II-Receptor Bonding

The tissue (rats lung) is homogenised in Tris-buffer (50 mMol Tris, 150 mMol NaCl, 5 mMol EDTA, pH 7.40) and centrifuged twice for 20 minutes at 20,000×g. The finished pellets are resuspended in incubating buffer [, (50 mMol Tris, 5 mMol MgC1$_2$, 0.2% BSA, pH 7.40) 1:75, based on the moist weight of the tissue. Each 0.1 ml of homogenate is incubated for 60 minutes at 37° C. with 50 pM [$^{125}$I]-angiotensin II (NEN, Dreieich, FRG) with increasing concentrations of the test substance in a total volume of 0.25 ml. Incubation is ended by rapid filtration through glass fibre filter mats. The filters are each washed with 4 ml of ice cold buffer (25 mMol Tris, 2.5 mMol MgCl$_2$, 0.1% BSA, pH 7.40). The bound radioactivity is measured using a gamma-counter. The corresponding IC$_{50}$ value is obtained from the dose-activity curve.

In the test described, substances A to D show the following IC$_{50}$ values:

| Substance | IC$_{50}$ [nM] |
| --- | --- |
| A | 46 |
| B | 30 |
| C | 230 |
| D | 420 |

In addition, compounds A to D were tested on conscious renally hypertensive rats for their effect after oral administration using methods known from the literature. At a dosage of 10 mg/kg these compounds exhibited a hypotensive effect.

Moreover, when the above-mentioned compounds were administered in a dose of 30 mg/kg i.v. no toxic side effects, e.g. no negative inotropic effects and no disorders in heart rhythm, were observed. The compounds are therefore well tolerated.

In view of their pharmacological properties, the new compounds and the physiologically acceptable addition salts thereof are suitable for the treatment of hypertension and cardiac insufficiency and also for treating ischaemic peripheral circulatory disorders, myocardial ischaemia (angina), for the prevention of the progression of cardiac insufficiency after myocardial infarction and for treating diabetic nephropathy, glaucoma, gastrointestinal diseases and bladder diseases.

The new compounds and the physiologically acceptable salts thereof are also suitable for treating pulmonary diseases, e.g. lung oedema and chronic bronchitis, for preventing arterial re-stenosis after angioplasty, for preventing thickening of blood vessel walls after vascular operations, and for preventing arteriosclerosis and diabetic angiopathy. In view of the effects of angiotensin on the release of acetyl-choline and dopamine in the brain, the new angiotensin antagonists are also suitable for alleviating central nervous system disorders, e.g. depression, Alzheimer's disease, Parkinson syndrome, bulimia and disorders of cognitive function.

The dosage required to achieve these effects in adults is appropriately, when administered intravenously, 20 to 100 mg, preferably 30 to 70 mg, and, when administered orally, 50 to 200 mg, preferably 75 to 150 mg, 1 to 3 times a day. For this purpose, the compounds of general formula I prepared according to the invention, optionally in conjunction with other active substances, such as hypotensives, diuretics and/or calcium antagonists, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, in conventional galenic preparations such as plain or coated tablets, capsules, powders, suspensions or suppositories.

Additional active substances which may be included in the combinations mentioned above might be, for example, bendroflumethiazide, chlorothiazide, hydrochlorothiazide, spironolactone, benzothiazide, cyclothiazide, ethacrinic acid, furosemide, metoprolol, prazosine, atenolol, propranolol, (di)hydralazine-hydrochloride, diltiazem, felodipin, nicardipin, nifedipin, nisoldipin and nitrendipin. The dosage for these active substances is appropriately 1/5 of the lowest recommended dose up to 1/1 of the normally recommended dose, i.e., for example, 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felodipine, 5 to 60 mg of nifedipin or 5 to 60 mg of nitrendipin.

The Examples which follow are intended to illustrate the invention:

EXAMPLE 1

(R,S)-2-Ethyl-8-methyl-5-[α-(2'-carboxybiphenyl-4-yl)-α-hydroxy-methyl]imidazo[1,2-a]pyridine a) 2-Ethyl-8-methyl-imidazo[1,2-a]pyridine 21.6 g (0.2 mol) of 2-amino-3-picoline were dissolved in 300 ml of 1,2-dimethoxyethane and combined with 33.2 g (0.2 Mol) of 1-methanesulphonyloxy-2-butanone. The reaction mixture was stirred for 3 days at ambient temperature. Then the solvent was evaporated off in vacuo. The residue was purified over a silica gel column (particle size: 0.063 to 0.02 mm), using as eluant methylene chloride to begin with, followed by mixtures of methylene chloride and ethanol of increasing polarity (2–4% ethanol). The uniform fractions were evaporated down in vacuo.

Yield: 7.8 g (24 % of theory),

Oil, $R_f$ value: 0.50 (silica gel; eluant: methylenechloride/ethanol=9:1).

b)
(R,S)-2-Ethyl-8-methyl-5-[α-(2'-(tert.-butyloxycarbonyl)-biphenyl-4-yl)-α-hydroxy-methyl]imidazo[1,2-a]pyridine 2.30 g (16 mMol) of 2-ethyl-8-methyl-imidazo[1,2-a]-pyridine are dissolved in 30 ml of absolute tetrahydrofuran and at −78° C. under nitrogen it is slowly combined with 10.4 ml of a 1.1 molar solution of n-butyllithium in hexane (16.6 mMol). The reaction mixture is stirred at −78° C. for 30 minutes then slowly heated to −20° C. It is then cooled again to −78° C. and a o solution of 4.7 g (16.6 mMol) of 4-(2'-tert.butyloxycarbonyl)phenyl-benzaldehyde in 15 ml of absolute tetrahydrofuran is added dropwise within 30 minutes. The mixture is stirred for 3 hours at 78° C. and then for 12 hours at ambient temperature. After the addition of 30 ml of saturated ammonium chloride solution it is extracted 4 times with 50 ml of ethyl acetate. The combined organic extracts are washed with saturated saline solution, dried over magnesium sulphate and concentrated by evaporation. The residue is purified over a silica gel column (particle size: 0.0630.02 mm), using as eluant methylene chloride to begin with, followed by mixtures of methylene chloride and ethanol of increasing polarity (2 to 5% ethanol). The uniform fractions are evaporated down in vacuo.

Yield: 3.70 g (52 % of theory),

Oil, $R_f$ value: 0.50 (silica gel; eluant: methylene chloride/ethanol=95:5).

c)
(R,S)-2-Ethyl-8-methyl-5-[α-(2'-carboxybiphenyl-4-yl)-α-hydroxy-methyl]imidazo1,2-a]pyridine 3.50 g (7.9 mMol) of (R,S)-2-ethyl-8-methyl-5-[α-(2'-(tert.butyloxycarbonyl)biphenyl-4-yl)-α-hydroxymethyl]imidazo[1,2-a]pyridine are dissolved in 25 ml of methylene chloride and combined with 5 ml of trifluoroacetic acid. The mixture is stirred for 12 hours at ambient temperature and then evaporated down. The residue is combined with 25 ml of water and dissolved by the addition of conc. ammonia. The precipitate formed after the addition of glacial acetic acid is suction filtered, washed with water and dried in vacuo at 60° C.

Yield: 0.49 g (16 % of theory),

Melting point: >250° C.

$C_{24}H_{22}N_2O_3$ (386.46); Calculated: C 74.59; H 5.74; N 7.25; Found: C 74.08; H 5.84., N 7.59

Mass spectrum: $M^+ = 386$.

EXAMPLE 2

(R,S)-2-Ethyl-5-[α-(2'-carboxybiphenyl-4-yl)-α-hydroxymethyl]imidazo[1,2-a]pyridine a) 2-Ethyl-imidazo[1,2-a]pyridine

Prepared analogously to Example 1a from 2-aminopyridine and 1-methanesulphonyloxy-2-butanone.

Yield: 34% of theory,

Oil, $R_f$ value: 0.30 (silica gel; eluant: methylene chloride/ethanol=95:5).

b)
(R,S)-2-Ethyl-5-[α-(2'-(tert.butyloxycarbonyl)biphenyl-4-yl)-α-hydroxy-methyl]imidazo[1,2-a]pyridine Prepared analogously to Example 1b from 2-ethylimidazo[1,2-a]-pyridine and 4-(2'-tert.butyloxycarbonyl)phenyl-benzaldehyde.

Yield: 23% of theory.

Oil, $R_f$ value: 0.15 (silica gel; eluant: methylene chloride/ethanol=95:5).

c)
(R,S)-2-Ethyl-5-[α-(2'-carboxybiphenyl-4-yl)-α-hydroxy-methyl]imidazo1,2-a]pyridine Prepared analogously to Example 1c from (R,S)-2-ethyl-5-[α-(2'-(tert.butyloxycarbonyl)biphenyl-4-yl)-α-hydroxymethyl]imidazo[1,2-a]pyridine and trifluoroacetic acid.

Yield: 38% of theory,

Melting point: 235° C.(decomposition)

$C_{23}H_{20}N_2O_3$ (372.43): Calculated: C 74.18; H 5.41; N 7.52., Found: C 74.21; H 5.4; N 7.18

Mass spectrum: M+ = 372.

EXAMPLE 3

2-Ethyl-5-[(2'-carboxybiphenyl-4-yl)carbonyl-]imidazo[1,2-a]-pyridine a)

2-Ethyl-5-[(2'-(tert.butyloxycarbonyl)biphenyl-4-yl)carbonyl]imidazo[1,2-a]pyridine 600 mg (1.4 mMol) of (R,S)-2-ethyl-5-[α-(2'-'(tert.butyloxycarbonyl)biphenyl-4-yl)-α-hydroxymethyl-]imidazo[1,2-a]pyridine are dissolved in 30 ml of chloroform and mixed with 2 g of manganese dioxide. The mixture is stirred for 24 hours at ambient temperature. It is then filtered, the filtrate is washed with methylene chloride and the combined organic phases are evaporated down. The residue is purified over a silica gel column (particle size: 0.063 to 0.02 mm), using as eluant methylene chloride to start with, followed by methylene chloride with 2.5% ethanol. The uniform fractions are evaporated down in vacuo.

Yield: 0.35 g (59% of theory),

Oil, $R_f$ value: 0.75 (silica gel; eluant: methylene chloride/ethanol=9:1).

b)

2-Ethyl-5-[(2'-carboxybiphenyl-4-yl)carbonyl-]imidazo[1,2-a]pyridine

Prepared analogously to Example 1c from 2-ethyl-5-[(2'-(tert.butyloxycarbonyl)biphenyl-4-yl)carbonyl]-imidazo[1,2-a]pyridine and trifluoroacetic acid.

Yield: 79% of theory,

Melting point: 115° C.

$C_{23}H_{18}N_2O_3$ (370.41) Calculated: C 74.58; H 4.90; N 7.56; Found: C 73.82; H 5.02; N 7.48

Mass spectrum: M+ = 370.

EXAMPLE 4

(R,S)-2-Ethyl-5-[α-(2'-carboxybiphenyl-4-yl)-α-acetoxymethyl]imidazo[1,2-a]pyridine a)

(R,S)-2-Ethyl-5-[α-(2'-(tert.butyloxycarbonyl)biphenyl-4-yl)-α-acetoxymethy]-imidazo[1,2-a]pyridine 350 mg (0.8 mMol) of (R,S)-2-ethyl-5-[α-(2'-(tert.butyloxycarbonyl)biphenyl-4-yl)-α-hydroxymethyl-]imidazo[1,2-a]pyridine are dissolved in 4 ml of aceticanhydride and heated to 100° C. for 30 minutes. Then the reaction mixture is evaporated down, the residue is combined with 10 ml of water and extracted with ethyl acetate. The combined organic phases are dried over magnesium sulphate and then evaporated down. The residue is reacted further without purification.

Yield 0.39 g (100% of theory),

Oil, $R_f$ value: 0.65 (silica gel; eluant: methylene chloride/ethanol=95:5).

b)

(R,S)-2-Ethyl-5-[α-(2'-carboxybiphenyl-4-yl)-α-acetoxy-methylimidazo[1,2-a]pyridine Prepared analogously to Example 1c from (R,S)-2-ethyl-5-α-[α-(2'-(tert.butyloxycarbonyl)biphenyl-4-yl)-α-acetoxymethyl]imidazo[1,2-a]pyridine and trifluoroacetic acid.

Yield: 51% of theory,

Melting point: 217°–218° C.

$C_{25}H_{22}N_2O_4$ (414.47); Calculated: C 72.45; H 5.35; N 6.76., Found: 72.23; H 5.0; N 6.89

Mass spectrum: M+ = 414.

EXAMPLE 5

(R,S)-2-Ethyl-8-methyl-5-[α-(2'-carboxybiphenyl-4-yl)-α-acetoxy-methyl]imidazo[1,2-a]pyridine a)

(R,S)-2-Ethyl-8-methyl-5-[α-(2'-tert.butyloxycarbonyl)-biphenyl-4-yl)-α-acetoxy-methyl]imidazo-[1,2-a]pyridine Prepared analogously to Example 4a from (R,S)-2-ethyl-8-methyl-5-[α-(2'-tert.butyloxycarbonyl)biphenyl-4-yl)-α-hydroxy-methyl]imidazo[1,2-a]pyridine and acetic anhydride.

Yield: 100% of theory,

Oil, $R_f$ value: 0.60 (silica gel; eluant: methylene chloride/ethanol=9:1).

b)

(R,S)-2-Ethyl-8-methyl-5-[α-(2'-carboxybiphenyl-4-yl)-α-acetoxy-methyl]imidazo[1,2-a]pyridine Prepared analogously to Example 1c from (R,S)-2-ethyl-8-methyl-5-[α-(2'-tert.butyloxycarbonyl)biphenyl-4-yl)-α-acetoxy-methyl]imidazo[1,2-a]pyridine and trifluoroacetic acid.

Yield: 58% of theory,

Melting point: 228°–230° C. $C_{26}H_{24}N_2O_4$ (428.49) Mass spectrum: M+ = 428.

EXAMPLE 6

(R,S)-2-Ethyl-8-methyl-5-[α-(2'-carboxybiphenyl-4-yl)-α-methoxy-methyl]imidazo[1,2-a]pyridine a)

(R,S)-2-Ethyl-8-methyl-5-[α-(2'-(tert.butyloxycarbonyl)-biphenyl-4-yl)-α-methoxy-methyl]-imidazo[1,2-a]pyridine 440 mg (1.0 mMol) of (R,S)-2-ethyl-8-methyl-5-[α-(2'-(tert.butyloxycarbonyl)biphenyl-4-yl)-α-hydroxymethyl]imidazo[1,2-a]pyridine are dissolved in 5 ml of dimethylformamide. After the addition of 130 mg (1.22 mMol) of potassium tert.butoxide the mixture is stirred for 30 minutes at ambient temperature. Then 170 mg (1.2 mMol) of methyliodide are added. The reaction mixture is then stirred for a further 5 hours at ambient temperature. After the addition of 10 ml of water it is extracted twice with ethyl acetate. The combined organic phases are washed with saturated sodium chloride solution, dried over magnesium sulphate and then evaporated down. The residue is purified over a silica gel column (particle size: 0.063 to 0.02 mm), using as eluant methylene chloride with 1.5% ethanol. The uniform fractions are evaporated down in vacuo.

Yield: 0.13 g (29% of theory),

Oil, $R_f$ value: 0.50 (silica gel; eluant: methylene chloride/ethanol=95:5).

b)

(R,S)-2-Ethyl-8-methyl-5-[α-(2'-carboxybiphenyl-4-yl)-α-methoxy-methyl]imidazo[1,2-a]pyridine Prepared analogously to Example 1c from (R,S)-2-ethyl-8-methyl-5-[α-(2'-(tert.butyloxycarbonyl)biphenyl-4-yl)-α-methoxy-methyl]imidazo[1,2-a]pyridine and trifluoroacetic acid.

Yield: 89% of theory,

Melting point: 120°–123° C.

$C_{25}H_{24}N_2O_3$ (400.48)
Mass spectrum: $M^+ = 400$.

EXAMPLE 7

2-Ethyl-8-methyl-5-[(2'-carboxybiphenyl-4-yl)-methyl-]imidazo[1,2-a]pyridine a)

(R,S)-2-Ethyl-8-methyl-5-[α-(2'-(tert.-butyloxycarbonyl)-biphenyl-4-yl)-α-(methylthiothiocarbonyloxy)-methyl]imidazo[1,2-a]pyridine 440 mg (1.0 mMol) of (R,S)-2-ethyl-8-methyl-5-[α-(2'-(tert.butyloxycarbonyl)biphenyl-4-yl)-α-hydroxymethyl]imidazo[1,2-a]pyridine are dissolved under nitrogen in 10 ml of absolute tetrahydrofuran and mixed with 5 mg of imidazole. After the addition of 72 mg (1.5 mMol) of (50%) sodium hydride the mixture is stirred for 20 minutes at ambient temperature. Then 228 mg (3.0 mMol) of carbon disulphide are added followed after 30 minutes by 253 mg (1.8 mMol) of methyliodide. Then the reaction mixture is stirred for a further 15 minutes at ambient temperature. After the addition of 3 drops of acetic acid, 20 ml of ether are added. The organic phase is washed with saturated sodium hydrogen carbonate solution and then with saturated sodium chloride solution, dried over magnesium sulphate and then evaporated down. The residue is further reacted without purification.

Yield: 0.57 g,

Oil, $R_f$ value: 0.55 (silica gel; eluant: methylene chloride/ethanol=95:5).

b)

2-Ethyl-8-methyl-5-[(2'tert.butyloxycarbonyl)biphenyl-4-yl)methyl]imidazo[1,2-a]pyridine 532 mg (1.0 mMol) of (R,S)-2-ethyl-8-methyl-5-[α-(2'-(tert.butyloxycarbonyl)biphenyl-4-yl)-α-(methylthiothiocarbonyloxy)-methyl]imidazo[1,2-a]pyridine are dissolved in 10 ml of toluene and combined under nitrogen with 437 mg (1.5 mMol) of tri-n-butyl tin hydride. The reaction mixture is refluxed for 18 hours. It is then evaporated down in vacuo and the residue is purified over a silica gel column (particle size: 0.063 to 0.02 mm). The eluant used is initially methylene chloride, followed by methylene chloride with 1 to 2.5% ethanol. The uniform fractions are evaporated down in vacuo.

Yield: 160 mg (38% of theory),

Oil, $R_f$ value: 0.40 (silica gel; eluant: methylene chloride/ethanol=95:5).

c)

2-Ethyl-8-methyl-5-[(2'-carboxybiphenyl-4-yl)methyl]-imidazo[1,2-a]pyridine

Prepared analogously to Example 1c from 2-ethyl-8-methyl-5-[(2'-tert.butyloxycarbonyl)biphenyl-4-yl)methyl]imidazo[1,2-a]pyridine and trifluoroacetic acid.

Yield: 77% of theory,
Melting point: 250° C.
$C_{24}H_{22}N_2O_2$ (370.46)
Mass spectrum: $M^+ = 370$.

EXAMPLE 8

(R,S)-2-Ethyl-8-methyl-5-[α-(2'-carboxybiphenyl-4-yl)-α-cyclohexylaminocarbonyloxy-methyl]imidazo[1,2-a]pyridine a)

(R,S)-2-Ethyl-8-methyl-5-[α-[2'-(tert.butyloxycarbonyl)-biphenyl-4-yl]-α-cyclohexylaminocarbonyloxy-methyl]imidazo[1,2-a]pyridine 440 mg (1.0 mMol) of (R,S)-2-ethyl-5-[α-[2'-(tert.butyloxycarbonyl)biphenyl-4-yl]-α-hydroxymethyl-]imidazo[1,2-a]pyridine and 500 mg (3.9 mMol) of cyclohexylisocyanate are dissolved in 5 ml of absolute pyridine and refluxed for 4 hours. The reaction mixture is then evaporated down. The residue is reacted further without purification.

b)

(R,S)-2-Ethyl-8-methyl-5-[α-(2'-carboxybiphenyl-4-yl)-α-cyclohexylaminocarbonyloxy-methyl]-imidazo1,2-a]pyridine Prepared analogously to Example 1c from (R,S)-2-ethyl-8-methyl-5-[α-[2'-(tert.butyloxycarbonyl)biphenyl-4-yl]-α-cyclohexylaminocarbonyloxy-methyl]imidazo[1,2-a]pyridine and trifluoroacetic acid.

Yield: 33% of theory,
Melting point: 243° C.(decomp)
$C_{31}H_{33}N_3O_4$ (511.63)
Mass spectrum: $M^+ = 511$.

EXAMPLE 9

(R,S)-2-Ethyl-8-methyl-5-[α-(2'-carboxybiphenyl-4-yl)-α-cyclohexylcarbonyloxy-methyl]imidazo[1,2-a]pyridine a)

(R,S)-2-Ethyl-8-methyl-5-[α-[2'-(tert.butyloxycarbonyl)-biphenyl-4-yl]-α-cyclohexylcarbonyloxymethyl]imidazo[1,2-a]pyridine Prepared analogously to Example 4a from (R,S)-2-ethyl-8-methyl-5-[α-[2'-(tert.butyloxycarbonyl)biphenyl-4-yl]-α-hydroxy-methyl]imidazo[1,2-a]pyridine and cyclohexylcarboxylic acid chloride.

Yield: 100% of theory, $R_f$ value: 0.50 (silica gel; eluant: ethyl acetate/petroleum ether=1:1).

b)

(R,S)-2-Ethyl-8-methyl-5-[α-(2'-carboxybiphenyl-4-yl)-α-cyclohexylcarbonyloxy-methyl]imidazo[1,2-a]pyridine Prepared analogously to Example 1c from (R,S)-2-ethyl-8-methyl-5-[α-[2'-(tert.butyloxycarbonyl)biphenyl-4-yl]-α-cyclohexylcarbonyloxy-methyl]imidazo[1,2-a]pyridine and trifluoroacetic acid.

Yield: 54% of theory,
Melting point: 243° C.(decomp)
$C_{31}H_{32}N_2O_4$ (496.61)
Mass spectrum: $M^+ = 496$.

EXAMPLE 10

(R,S)-2-n-Propyl-8-methyl-5-[α-(2'-carboxybiphenyl-4-yl)-α-hydroxy-methyl]imidazo[1,2-a]pyridine-hydrate a)
2-n-Propyl-3-ethoxycarbonyl-8-methyl-imidazo[1,2-a]-pyridine 2.3 g (11.9 mMol) of ethyl 2-chloro-3-oxo-hexane carboxylate and 2.6 g (23.8 mMol) of 2-amino-3-picoline are dissolved in 10 ml of ethyleneglycol-dimethylether and refluxed for 3 days. Then the solvent is evaporated off in vacuo and the residue is taken up in water/ethyl acetate 1:1. After the extraction the organic phase is separated off, washed with saturated saline solution, dried over magnesium sulphate and evaporated down. The residue is purified over a silica gel column (particle size: 0.063 to 0.02 mm), using as eluant mixtures of petroleum ether/ethyl acetate of increasing polarity (85:15, 80:20 and 1:1). The uniform fractions are evaporated down in vacuo.

Yield: 2.0 g (69% of theory),
Melting point: 68°–70° C.

b)
2-n-Propyl-3-carboxy-8-methyl-imidazo[1,2-a]pyridine 21.0 g (86 mMol) of 2-n-propyl-3-ethoxycarbonyl-8-methylimidazo[1,2-a]pyridine are dissolved in 200 ml of ethanol, mixed with 100 ml of 2N sodium hydroxide solution and stirred for 4 days at ambient temperature. The solvent is evaporated off in vacuo at 40° C., the residue is diluted with water and combined with 20 g of ammonium chloride. The pH is adjusted to 6.5 by the addition of glacial acetic acid. After 2 hours, the precipitate formed is suction filtered, washed with water and dried in vacuo at 40° C.

Yield: 17.3 g (92% of theory),
Melting point: 164°–165° C.

c) 2-n-Propyl-8-methyl-imidazo[1,2-a]pyridine 17.3 g (79 mMol) of 2-n-propyl-3-carboxy-8-methylimidazo[1,2-a]pyridine are dissolved in 200 ml of diethyleneglycol-dimethylether and heated to 160° C. for one hour. After cooling the solution is poured onto 1.2 liters of ice water and extracted with ethyl acetate. The combined organic phases are washed with sodium hydrogen carbonate solution and with water, dried over magnesium sulphate and evaporated down in vacuo. The residue is taken up in 100 ml of ether and mixed with 50 g of silica gel and 10 g of activated charcoal. It is then filtered and the filtrate is evaporated down.

Yield: 13.8 g (100% of theory),
Oil, $R_f$ value: 0.50 (silica gel; eluant: ethyl acetate).

d)
(R,S)-2-n-propyl-8-methyl-5-[α-(2'-(tert.butyloxycarbonyl)biphenyl-4-yl)-α-hydroxy-methyl]imidazo[1,2-a]pyridine Prepared analogously to Example 1b from 2-n-propyl-8-methyl-imidazo[1,2-a]pyridine and 4-(2'-tert.butyloxycarbonyl)phenyl-benzaldehyde.

Yield: 34% of theory,
$R_f$ value: 0.60 (silica gel; eluant: ethyl acetate/ethanol = 19:1).

(R,S)-2-n-Propyl-8-methyl-5-[α-(2'-carboxybiphenyl-4-yl)-α-hydroxy-methyl]imidazo[1,2-a]pyridine-hydrate Prepared analogously to Example 1c from (R,S)-2-n-propyl-8-methyl-5-[α-[2'-(tert.butyloxycarbonyl)-biphenyl-4-yl)-α-hydroxy-methyl]imidazo[1,2-a]pyridine and trifluoroacetic acid.

Yield: 46% of theory,
Melting point: from 190° C.(decomp)
$C_{25}H_{24}N_2O_3 \times H_2O$ (418.50)
Calculated: C 71.75;. H 6.26; N 6.69; Found: C 72.0; H 6.14; N 7.33
Mass spectrum: M+ = 400.

EXAMPLE 11

(R,S)-2-n-Propyl-8-methyl-5-[α-(2'-carboxybipheny 1-4-yl)-α-benzyloxy-methyl]imidazo[1,2-a]pyridinesemihydrate a)
(R,S)-2-n-Propyl-8-methyl-5-[α-(2'-tert.-butyloxycarbonyl)biphenyl-4-yl)-α-benzyloxymethyl]imidazo1,2-a]pyridine-semihydrate Prepared analogously to Example 4a from (R,S)-2-n-propyl-8-methyl-5-[α-(2'-(tert.butyloxycarbonyl)-biphenyl-4-yl)-α-hydroxy-methyl]imidazo[1,2-a]pyridine and benzylbromide.

Yield: 33% of theory,
$R_f$ value: 0.45 (silica gel; eluant: ethyl acetate/petroleum ether = 1:1).

b)
(R,S)-2-n-Propyl-8-methyl-5-[α-(2'-carboxybiphenyl-4-yl)-α-benzyloxy-methyl]imidazo[1,2-a]pyridine-semihydrate Prepared analogously to Example 1c from (R,S)-2-n-propyl-8-methyl-5-[α-(2'-(tert.butyloxycarbonyl)-biphenyl-4-yl)-α-benzyloxy-methyl]imidazo[1,2-a]pyridine and trifluoroacetic acid.

Yield: 80% of theory,
Melting point: 113°–115° C.
$C_{32}H_{30}N_2O_3 \times 0.5\ H_2O$ (499.62)
Calculated: C 76.93; H 6.25; N 5.61; Found: C 77.25; H 6.40.; N 5.67
Mass spectrum: M+ = 490.

EXAMPLE 12

(R,S)-2-n-Propyl-8-methyl-5-[α-(2'-carboxybiphenyl-4-yl)-α-(2-pyridyl)methyloxy-methyl]imidazo[1,2-a]-pyridine-semihydrate Prepared analogously to Example 1c from (R,S)-2-n-propyl-8-methyl-5-[α-(2'-tert.butoxycarbonyl)biphenyl-α-(2-pyridyl)methyloxy-methyl]imidazo[1,2-a]pyridine and trifluoroacetic acid.

Yield: 68% of theory,
Melting point: 182°–184° C.
$C_{31}H_{29}N_3O_3 \times 0.5\ H_2O$ (500.61))
Calculated: C 74.38; H 6.04., N 8.39; Found: C 74.91; H 6.33, N 8.00
Mass spectrum: M+ = 491.

EXAMPLE 13

(R,S)-2-Ethyl-8-methyl-5-[α-(2'-carboxybiphenyl-4-yl)-α-benzyloxy-methyl]-imidazo[1,2-a]pyridine Prepared analogously to Example 1c from (R,S)-2-ethyl-8-methyl-5-[α-(2'-tert.butyloxycarbonyl)biphenyl-4-yl)-α-benzyloxy-methyl]-imidazo[1,2-a]pyridine and trifluoroacetic acid.

Yield: 17% of theory,
Melting point: 226° C.(decomp)
$C_{31}H_{28}N_2O_3$ (476.58)

Mass spectrum: M+ = 476.

EXAMPLE 14

2-n-Propyl-8-methyl-5-[α-(2'-carboxybiphenyl-4-yl)-α-ethoxycarbonylmethoxy-methyl]-imidazo[1,2-a]pyridine-semihydrate Prepared analogously to Example 1c from 2-n-propyl-8-methyl-5-[α-(2'-tert.butyloxycarbonyl)-α-ethoxycarbonylmethoxy-methyl]-imidazo[1,2-a]pyridine and trifluoroacetic acid.

Yield: 39% of theory,
Melting point: 115°–120° C.(sinters from 85° C.)
$C_{29}H_{30}N_2O_5 \times 0.5 H_2O$ (486.58)
Calculated: C 70.29; H 6.31; N 5.65; Found: C 70.09; H 6.52; N 5.40
Mass spectrum: M+ = 486.

EXAMPLE 15

2-Ethyl-8-methyl-5-[(2'-carboxybiphenyl-4-yl)-methyl]imidazo[1,2-a]pyridine

To a mixture of 20 ml of trifluoroacetic acid and 2.35 g (62 mMol) of sodium borohydride is added dropwise, at 5° C., a solution of 1.30 g (2.85 mMol) of (R,S)-2-ethyl-8-methyl-5-[α-(2'-tert.butyloxycarbonyl-biphenyl-4-yl)-α-hydroxy-methyl]imidazo[1,2-a]pyridine in 20 ml of methylene chloride. The suspension thus formed is stirred for 22 hours at ambient temperature. Then 1.0 g (2.6 mMol) of sodium borohydride and 20 ml of methylene chloride are added and the mixture is stirred for a further 6 hours at ambient temperature. The reaction mixture is combined with ice water and extracted with methylene chloride. The organic phase is washed with water, dried over magnesium sulphate and evaporated down. The residue is purified over a silica gel column (particle size: 0.063–0.02 mm) using as eluant methylene chloride/methanol 9:1 and 3:1. The uniform fractions are evaporated down in vacuo.

Yield: 0.1 g (9% of theory),
Melting point: 257°–260° C.(decomp.)

$C_{25}H_{24}N_2O_2$ (384.48))

Calc.×0.75 $H_2O$: C 75.45; H 6.46; N 7.04; Found: C 75.52; H 6.56; N 6.72
Mass spectrum: M+ = 384

EXAMPLE 16

2-Ethyl-5-[4-(2-carboxyphenyl)phenoxy]imidazo[1,2-a]pyridine a) 2-Ethyl-5-chloro-imidazo[1,2-a]pyridine

Prepared analogously to Example 1a from 2-chloro-6-aminopyridine and 1-chloro-2-butanone.

Yield: 44% of theory,
Oil, $R_f$ value: 0.40 (silica gel; eluant: methylene chloride/xylene=1:1)

b) 2-Ethyl-5-[4-(2-methoxycarbonyl)phenyl]-phenoxyl]imidazo[1,2-a]pyridine 1.0 g (5.5 mMol) of 2-ethyl-5-chloro-imidazo[1,2-a]pyridine, 685 mg of potassium tert.butoxide and 1.50 g (6,6 mMol) of 2'-methoxy-carbonyl-4-hydroxy-biphenyl are dissolved in 15 ml of dimethylsulphoxide and stirred at ambient temperature for 24 hours. Then the reaction mixture is heated to 80° C. for a further 2 hours. After cooling, it is poured onto ice water and extracted twice with 50 ml ethyl acetate. The combined organic phases are washed with water and saturated sodium chloride solution, dried over sodium sulphate and evaporated down. The residue is purified over a silica gel column (particle size: 0.063–0.02 mm) using as eluant methylene chloride/ethanol 99:1 and 49:1 . The uniform fractions are evaporated down in vacuo.

Yield: 1.26 g (63% of theory),
Oil, $R_f$ value: 0.35 (silica gel; eluant: methylethylketone/xylene=1:1)

c) 2-Ethyl-5-[4-(2-carboxyphenyl)phenoxy]imidazo[1,2-a]pyridine 1.25 g (3.3 mMol) of 2-ethyl-5-[4-(2-methoxycarbonyl)phenyl]phenoxy]imidazo[1,2-a]pyridine are dissolved in 25 ml of ethanol, mixed with 15 ml of 2N sodium hydroxide solution and refluxed for 1 hour. After cooling and the addition of 15 ml of water the methanol is distilled off in vacuo and the aqueous phase is extracted with ethyl acetate. The aqueous phase is adjusted to pH 6 with hydrochloric acid. The crystalline residue is suction filtered in the cold and dried.

Yield: 830 mg (69% of theory),
Melting point: 261°–263° C.
$C_{22}H_{18}N_2O_3$ (358.40):
Calculated: C 73.73., H 5.06., N 7.82; Found: C 73.60; H 5.09; N 7.78

EXAMPLE 17

2-n-Propyl-8-methyl-5-[α-(2'-carboxybiphenyl-4-yl)-α-(2-carboxy-ethylcarbonyloxy)methyl]imidazo[1,2-a]pyridinedihydrate a) 2-n-Propyl-8-methyl-5-[α-(2'-(tert.butoxycarbonyl)-biphenyl-4-yl)-α-(2-carboxy-ethylcarbonyloxy)methyl]-imidazo[1,2-a]pyridine Prepared analogously to Example 4a from 2-n-propyl-8-methyl-5-[α-(2'-(tert.butoxycarbonyl)biphenyl-4-yl)-α-hydroxy-methyl]imidazo[1,2-a]pyridine and succinic acid anhydride.

Yield: 52% of theory,
Melting point: 101° C. (decomp.)

b) 2-n-Propyl-8-methyl-5-[α-(2'-carboxybiphenyl-4-yl)-α-(2-carboxy-ethylcarbonyloxy)methyl]imidazo[1,2-a]pyridine-dihydrate Prepared analogously to Example 1c from 2-n-propyl-8-methyl-5-[α-(2'-(tert.butoxycarbonyl)biphenyl-4-yl)-α-(2-carboxy-ethylcarbonyloxy)methyl]imidazo[1,2-a]-pyridine and trifluoroacetic acid.

Yield: 78% of theory
Melting point: from 100° C. (decomp.)
$C_{28}H_{28}N_2O_6 \cdot 2 \times H_2O$ (536.59): Calc.×2 $H_2O$: C 64.91;H 6.01;N 5.22; Found: C 65.29; H 6.0; N 5.21

The following compounds may be obtained analogously by the processes of the present application:

(1)  (R,S)-2-ethyl-3,8-dimethyl-5-[α-(2'-carboxybiphenyl-4-yl)-α-hydroxy-methyl]imidazo[1,2-a]pyridine (2)  (R,S)-2-ethyl-3-bromo-8-methyl-5-[α-(2'-carboxybiphenyl-4-yl)-α-hydroxy-methyl]imidazo[1,2-a]pyridine (3) (R,S)-2-ethyl-7-methyl-5-[α-(2'-carboxybiphenyl-4-yl)-α-hydroxy-methyl]imidazo[1,2-a]pyridine 4) (R,S)-2-ethyl-6-methyl-5-[α-(2'-carboxybiphenyl-4-yl)-α-hydroxy-methyl]imidazo[1,2-a]pyridine (5) (R,S)-2-ethyl-6,8-dimethyl-5-[α-(2'-carboxybiphenyl-4-yl)-α-hydroxy-methyl]imidazo[1,2-a]pyridine
(6) (R,S)-2-ethyl-7-trifluoromethyl-5-[α-(2'-carboxybiphenyl-4-yl)-α-hydroxy-methyl]imidazo[1,2-a]pyridine
(7) (R,S)-2-ethyl-6,8-dimethyl-5-[α-(2'-(1H-tetrazol-5-yl)biphenyl-4-yl)-α-hydroxy-methyl]imidazo[1,2-a]pyridine
(8) (R,S)-2-ethyl-8-methyl-5-[α-(2'-(1H-tetrazol-5-yl)biphenyl-4-yl)-α-hydroxy-methyl]imidazo[1,2-a]pyridine
(9) (R,S)-2-ethyl-8-methyl-5-[α-(2'-carboxybiphenyl-4-yl)-α-ethoxy-methyl]imidazo[1,2-a]pyridine
(10) (R,S)-2-ethyl-8-methyl-5-[α-(2'-carboxybiphenyl-4-yl)-α-n-propyloxy-methyl]imidazo[1,2-a]pyridine
(11) (R,S)-2-ethyl-8-methyl-5-[α-(2'-carboxybiphenyl-4-yl)-α-iaobutyloxy-methyl]imidazo[1,2-a]pyridine
(12) (R,S)-2-ethyl-8-methyl-5-[e-(2'-(1H-tetrazol-5-yl)biphenyl-4-yl)-α-methoxy-methyl]imidazo[1,2-a]pyridine
(13) (R,S)-2-ethyl-8-methyl-5-[α-(2'-carboxybiphenyl-4-yl)-α-propionyloxy-methyl]imidazo[1,2-a]pyridine
(14) (R,S)-2-ethyl-8-methyl-5-[α-(2'-carboxybiphenyl-4-yl)-α-butyryloxy-methyl]imidazo[1,2-a]pyridine
(15) (R,S)-2-ethyl-8-methyl-5-[α-(2'-carboxybiphenyl-4-yl)-α-pivaloyloxy-methyl]imidazo[1,2-a]pyridine
(16) (R,S)-2-ethyl-8-methyl-5-[α-(2'-carboxybiphenyl-4-yl)-α-benzoyloxy-methyl]imidazo[1,2-a]pyridine
(17) (R,S)-2-ethyl-8-methyl-5-[α-(2'-carboxybiphenyl-4-yl)-α-phenylmethylcarbonyloxy-methyl]imidazo[1,2-a]pyridine
(18) (R,S)-2-ethyl-8-methyl-5-[α-(2'-(1H-tetrazol- 5-yl)biphenyl-4-yl)-α-pivaloyloxy-methyl]imidazo[1,2-a]pyridine
(19) (R,S)-2-ethyl-8-methyl-5-[α-(2'-carboxybiphenyl-4-yl)-α-(n-butylamino-carbonyloxy)methyl-]imidazo[1,2-a]pyridine
(20) (R,S)-2-ethyl-8-methyl-5-[α-(2'-carboxybiphenyl-4-yl)-α-(phenylamino-carbonyloxy)methyl-]imidazo[1,2-a]pyridine
(21) (R,S)-2-ethyl-8-methyl-5-[α-(2'-carboxybiphenyl-4-yl)-α-(benzylamino-carbonyloxy)methyl-]imidazo[1,2-a] pyridine
(22) 2-ethyl-8-methyl-5-[(2'-(1H-tetrazol-5-yl)biphenyl4-yl)methyl]imidazo[1,2-a]pyridine
(23) (R,S)-2-ethyl-8-methyl-5-[α-(2'-(1H-tetrazol-5-yl)biphenyl-4-yl)-α-(cyclohexylaminocarbonyloxy)-methyl]imidazo[1,2-a]pyridine
(24) (R,S)-2-n-propyl-3,8-dimethyl-5-[α-(2'-carboxybiphenyl-4-yl)-α-hydroxy-methyl]imidazo[1,2-a]pyridine
(25) (R,S)-2-n-propyl-3-bromo-8-methyl-5-[α-(2'-carboxybiphenyl-4-yl)-α-hydroxy-methyl]imidazo[1,2-a]pyridine
(26) (R,S)-2-n-propyl-7-methyl-5-[α-(2'-carboxybiphenyl-4-yl)-α-hydroxy-methyl]imidazo[1,2-a]pyridine
(27) (R,S)-2-n-propyl-6-methyl-5-[α-(2'-carboxybiphenyl-4-yl)-α-hydroxy-methyl]imidazo[1,2-a]pyridine
(28) (R,S)-2-n-propyl-6,8-dimethyl-5-[α-(2'-carboxybiphenyl-4-yl)-α-hydroxy-methyl]imidazo[1,2-a]pyridine
(29) (R,S)-2-n-propyl-7-trifluoromethyl-5-[α-(2'-carboxybiphenyl-4-yl)-α-hydroxy-methyl]imidazo[1,2-a]pyridine
(30) (R,S)-2-n-propyl-6,8-dimethyl-5-[α-(2'-(1H-tetrazol-5-yl)biphenyl-4-yl)-α-hydroxy-methyl]imidazo[1,2-a]pyridine
(31) (R,S)-2-n-propyl-8-methyl-5-[α-(2'-(1H-tetrazol-5-yl)biphenyl-4-yl)-α-hydroxy-methyl]imidazo[1,2a]pyridine
(32) (R,S)-2-n-propyl-8-methyl-5-[α-(2'-carboxybiphenyl-4-yl)-α-ethoxy-methyl]imidazo[1,2-a]pyridine
(33) (R,S)-2-n-propyl-8-methyl-5-[α-(2'-carboxybiphenyl-4-yl)-α-n-propyloxy-methyl]imidazo[1,2-a]pyridine
(34) (R,S)-2-n-propyl-8-methyl-5-[α-(2'-carboxybiphenyl-4-yl)-α-isobutyloxy-methyl]imidazo[1,2-a]pyridine
(35) (R,S)-2-n-propyl-8-methyl-5-[α-(2'-(1H-tetrazol-5-yl)-biphenyl-4-yl)-α-methoxy-methyl]imidazo[1,2-a]pyridine
(36) (R,S)-2-n-propyl-8-methyl-5-[α-(2'-carboxybiphenyl-4-yl)-α-propionyloxy-methyl]imidazo[1,2-a]pyridine
(37) (R,S)-2-n-propyl-8-methyl-5-[α-(2'-carboxybiphenyl-4-yl)-α-butyryloxy-methyl]imidazo[1,2-a]pyridine
(38) (R,S)-2-n-propyl-8-methyl-5-[α-(2'-carboxybiphenyl-4-yl)-α-pivaloyloxy-methyl]imidazo[1,2-a]pyridine
(39) (R,S)-2-n-propyl-8-methyl-5-[α-(2'-carboxybiphenyl-4-yl)-α-cyclohexylcarbonyloxy-methyl-]imidazo[1,2-a]pyridine
(40) (R,S)-2-n-propyl-8-methyl-5-[α-(2'-carboxybiphenyl-4-yl)-α-phenylmethylcarbonyloxy-methyl-]imidazo[1,2-a]pyridine
(41) (R,S)-2-n-propyl-8-methyl-5-[α-(2'-(1H-tetrazol-5-yl)-biphenyl-4-yl)-α-pivaloyloxy-methyl]imidazo[1,2-a]pyridine
(42) (R,S)-2-n-propyl-8-methyl-5-[α-(2'-carboxybiphenyl- 4-yl)-α-(n-butylamino-carbonyloxy)methyl-]imidazo[1,2-a]pyridine
(43) (R,S)-2-n-propyl-8-methyl-5-[α-(2'-carboxybiphenyl-4-yl)-α-(phenylamino-carbonyloxy)methyl-]imidazo[1,2-a]pyridine
(44) (R,S)-2-n-propyl-8-methyl-5-[α-(2'-carboxybiphenyl-4-yl)-α-(cyclohexylamino-carbonyloxy)methyl-]imidazo[1,2-a]-pyridine
(45) (R,S)-2-n-propyl-8-methyl-5-[α-(2'-carboxybiphenyl-4-yl)-α-(benzylamino-carbonyloxy)methyl-]imidazo[1,2-a]pyridine
(46) 2-n-propyl-8-methyl-5-[(2'-(1H-tetrazol-5-yl)biphenyl-4-yl)methyl]imidazo[1,2-a]pyridine
(47) (R,S)-2-n-propyl-8-methyl-5-[α-(2'-(1H-tetrazol-5-yl)-biphenyl-4-yl)-α-(cyclohexylaminocarbonyloxy)-methyl]imidazo[1,2-a]pyridine
(48) (R,S)-2-cyclopropyl-3,8-dimethyl-5-[α-(2'-carboxybiphenyl-4-yl)-α-hydroxy-methyl]imidazo[1,2-a]pyridine
(49) (R,S)-2-cyclopropyl-3-bromo-8-methyl-5-[α-(2'-carboxybiphenyl-4-yl)-α-hydroxy-methyl-]imidazo[1,2-a]pyridine
(50) (R,S)-2-cyclopropyl-7-methyl-5-[α-(2'-carboxybiphenyl-4-yl)-α-hydroxy-methyl]imidazo[1,2-a]pyridine
(51) (R,S)-2-cyclopropyl-6-methyl-5-[α-(2'-carboxybiphenyl-4-yl)-α-hydroxy-methyl]imidazo[1,2-a]pyridine
(52) (R,S)-2-cyclopropyl-6,8-dimethyl-5-[α-(2' carboxybiphenyl-4-yl)-α-hydroxy-methyl]imidazo[1,2-a]pyridine
(53) (R,S)-2-cyclopropyl-7-trifluoromethyl-5-[α-(2'-carboxybiphenyl-4-yl)-α-hydroxy-methyl]imidazo[1,2-a]pyridine

(54) (R,S)-2-cyclopropyl-6,8-dimethyl-5-[α-(2'-(1H-tetrazol-5-yl)biphenyl-4-yl)-α-hydroxy-methyl]imidazo[1,2-a]pyridine
(55) (R,S)-2-cyclopropyl-8-methyl-5-[α-(2'-(1H-tetrazol-5-yl)biphenyl-4-yl)-α-hydroxy-methyl]imidazo[1,2-a]pyridine
(56) (R,S)-2-cyclopropyl-8-methyl-5-[α-(2'-carboxybiphenyl-4-yl)-α-ethoxy-methyl]imidazo[1,2-a]pyridine
(57) (R,S)-2-cyclopropyl-8-methyl-5-[α-(2'-carboxybiphenyl-4-yl)-α-n-propyloxy-methyl]imidazo[1,2-a]pyridine
(58) (R,S)-2-cyclopropyl-8-methyl-5-[α-(2'-carboxybiphenyl-4-y )-α-isobutyloxy-methyl]imidazo[1,2-a]pyridine
(59) (R,S)-2-cyclopropyl-8-methyl-5-[α-(2'-(1H-tetrazol-5-yl)biphenyl-4-yl)-α-methoxy-methyl]imidazo[1,2-a]pyridine
(60) (R,S)-2-cyclopropyl-8-methyl-5-[α-(2'-carboxybiphenyl-4-yl)-α-propionyloxy-methyl imidazo[1,2-a]pyridine
(61) (R,S)-2-cyclopropyl-8-methyl-5-[α-(2' carboxybiphenyl-4-yl)-α-butyryloxy-methyl]imidazo[1,2-a]pyridine
(62) (R,S)-2-cyclopropyl-8-methyl-5-[α-(2'-carboxybiphenyl-4-yl)-α-pivaloyloxy-methyl]imidazo[1,2-a]pyridine
(63) (R,S)-2-cyclopropyl-8-methyl-5-[α-(2'-carboxybiphenyl-4-yl)-α-cyclohexylcarbonyloxymethyl]imidazo[1,2-a]pyridine
(64) (R,S)-2-cyclopropyl-8-methyl-5-[α-(2'-carboxybiphenyl-4-yl)-α-benzoyloxy-methyl]imidazo[1,2-a]pyridine
(65) (R,S)-2-cyclopropyl-8-methyl-5-[α-(2'-carboxybiphenyl-4-yl)-α-phenylmethylcarbonyloxymethyl]imidazo[1,2-a]pyridine
(66) (R,S)-2-cyclopropyl-8-methyl-5-[α-(2'-(1H-tetrazol-5-yl)biphenyl-4-yl)-α-pivaloyloxy-methyl]imidazo[1,2-a]pyridine
(67) (R,S)-2-cyclopropyl-8-methyl-5-[α-(2'-carboxybiphenyl-4-yl)-α-(n-butylamino-carbonyloxy)methyl]imidazo[1,2-a]pyridine
(68) (R,S)-2-cyclopropyl-8-methyl-5-[α-(2'-carboxybiphenyl-4-yl)-α-(phenylamino-carbonyloxy)methyl]imidazo[1,2-a]pyridine
(69) (R,S)-2-cyclopropyl-8-methyl-5-[α-(2'-carboxybiphenyl-4-yl)-α-(cyclohexylamino-carbonyloxy)methyl]imidazo[1,2-a]pyridine
(70) (R,S)-2-cyclopropyl-8-methyl-5-[α-(2'-carboxybiphenyl-4-yl)-α-(benzylamino-carbonyloxy)methyl imidazo[1,2-a]pyridine
(71) 2-cyclopropyl-8-methyl-5-[(2'-(1H-tetrazol-5-yl)biphenyl-4-yl)methyl]imidazo[1,2-a]pyridine
(72) (R,S)-2-cyclopropyl-8-methyl-5-[α-(2'-(1H-tetrazol-5-yl)biphenyl-4-yl)-α-(cyclohexylaminocarbonyloxy)methyl]imidazo[1,2-a]pyridine
(73) (R,S)-2-n-butyl-3,8-dimethyl-5-[α-(2'-carboxybiphenyl-4-yl)-α-hydroxy-methyl]imidazo[1,2-a]pyridine
(74) (R,S)-2-n-butyl-3-bromo-8-methyl-5-[α-(2'-carboxybiphenyl-4-yl)-α-hydroxy-methyl]imidazo[1,2-a]pyridine
(75) (R,S)-2-n-butyl-7-methyl-5-[α-(2'-carboxybiphenyl-4-yl)-α-hydroxy-methyl]imidazo[1,2-a]pyridine
(76) (R,S)-2-n-butyl-6-methyl-5-[α-(2'-carboxybiphenyl-4-yl)-α-hydroxy-methyl]imidazo[1,2-a]pyridine
(77) (R,S)-2-n-butyl-6,8-dimethyl-5-[α-(2'-carboxybiphenyl-4-yl)-α-hydroxy-methyl]imidazo[1,2-a]pyridine
(78) (R,S)-2-n-butyl-7-trifluoromethyl-5-[α-(2'-carboxybiphenyl-4-yl)-α-hydroxy-methyl]imidazo[1,2-a]pyridine
(79) (R,S)-2-n-butyl-6,8-dimethyl-5-[α-(2'-(1H-tetrazol-5-yl)biphenyl-4-yl)-α-hydroxy-methyl]imidazo[1,2-a]pyridine
(80) (R,S)-2-n-butyl-8-methyl-5-[α-(2'-(1H-tetrazol-5-yl)-biphenyl-4-yl)-α-hydroxy-methyl]imidazo[1,2-a]pyridine
(81) (R,S)-2-n-butyl-8-methyl-5-[α-(2'-carboxybiphenyl-4-yl)-α-ethoxy-methyl]imidazo[1,2-a]pyridine
(82) (R,S)-2-n-butyl-8-methyl-5-[α-(2'-carboxybiphenyl-4-yl)-α-n-propyloxy-methyl]imidazo[1,2-a]pyridine
(83) (R,S)-2-n-butyl-8-methyl-5-[α-(2'-carboxybiphenyl-4-yl)-α-isobutyloxy-methyl]imidazo[1,2-a]pyridine
(84) (R,S)-2-n-butyl-8-methyl-5-[α-(2'-(1H-tetrazol-5-yl)biphenyl-4-yl)-α-methoxy-methyl]imidazo[1,2-a]pyridine
(85) (R,S)-2-n-butyl-8-methyl-5-[α-(2'-carboxybiphenyl-4-yl)-α-propionyloxy-methyl]imidazo[1,2-a]pyridine
(86) (R,S)-2-n-butyl-8-methyl-5-[α-(2'-carboxybiphenyl-4-yl)-α-butyryloxy-methyl]imidazo[1,2-a]pyridine
(87) (R,S)-2-n-butyl-8-methyl-5-[α-(2'-carboxybiphenyl-4-yl)-α-pivaloyloxy-methyl]imidazo[1,2-a]pyridine
(88) (R,S)-2-n-butyl-8-methyl-5-[α-(2'-carboxybiphenyl-4-yl)-α-cyclohexylcarbonyloxy-methyl]imidazo[1,2-a]pyridine
(89) (R,S)-2-n-butyl-8-methyl-5-[α-(2'-carboxybiphenyl-4-yl)-α-benzoyloxy-methyl]imidazo[1,2-a]pyridine
(90) (R,S)-2-n-butyl-8-methyl-5-[α-(2'-carboxybiphenyl-4-yl)-α-phenylmethylcarbonyloxy-methyl]imidazo[1,2-a]pyridine
(91) (R,S)-2-n-butyl-8-methyl-5-[α-(2'-(1H-tetrazol-5-yl)-biphenyl-4-yl)-α-pivaloyloxy-methyl]imidazo[1,2-a]pyridine
(92) (R,S)-2-n-butyl-8-methyl-5-[α-(2'-carboxybiphenyl-4-yl)-α-(n-butylamino-carbonyloxy)methyl]imidazo[1,2-a]pyridine
(93) (R,S)-2-n-butyl-8-methyl-5-[α-(2'-carboxybiphenyl-4-yl)-α-(phenylamino-carbonyloxy)methyl]imidazo[1,2-a]pyridine
(94) (R,S)-2-n-butyl-8-methyl-5-[α-(2'-carboxybiphenyl-4-yl)-α-(cyclohexylamino-carbonyloxy)methyl]imidazo[1,2-a]pyridine
(95) (R,S)-2-n-butyl-8-methyl-5-[α-(2'-carboxybiphenyl-4-yl)-α-(benzylamino-carbonyloxy)methyl]imidazo[1,2-a]pyridine
(96) 2-n-butyl-8-methyl-5-[(2'-(1H-tetrazol-5-yl) biphenyl-4-yl)methyl]imidazo[1,2-a]pyridine
(97) (R,S)-2-n-butyl-8-methyl-5-[α-(2'-(1H-tetrazol-5-yl)-biphenyl-4-yl)-α-(cyclohexylaminocarbonyloxy)methyl]imidazo[1,2-a]pyridine
(98) (R,S)-2-methoxy-3,8-dimethyl-5-[α-(2'-carboxybiphenyl-4-yl)-α-hydroxy-methyl]imidazo[1,2-a]pyridine
(99) (R,S)-2-methoxy-3-bromo-8-methyl-5-[α-(2'-carboxybiphenyl-4-yl)-α-hydroxy-methyl]imidazo[1,2-a]pyridine (100) (R,S)-2-methoxy-7-methyl-5-[α-(2'-carboxybiphenyl-4-yl)-α-hydroxy-methyl]imidazo[1,2-a]pyridine
(101) (R,S)-2-methoxy-6-methyl-5-[α-(2'-carboxybiphenyl-4-yl)-α-hydroxy-methyl]imidazo[1,2-a]pyridine
(102) (R,S)-2-methoxy-6,8-dimethyl-5-[α-(2'-carboxybiphenyl-4-yl)-α-hydroxy-methyl]imidazo[1,2-a]pyridine
(103) (R,S)-2-methoxy-7-trifluoromethyl-5-[α-(2'-carboxybiphenyl-4-yl)-α-hydroxy-methyl]imidazo[1,2-a]pyridine
(104) (R,S)-2-methoxy-6,8-dimethyl-5-[α-(2'-(1H-tetrazol-5-yl)biphenyl-4-yl)-α-hydroxymethyl]imidazo[1,2-a]pyridine
(105) (R,S)-2-methoxy-8-methyl-5-[α-(2'-(1H-tetrazol-5-yl)biphenyl-4-yl)-α-hydroxy-methyl]imidazo[1,2-a]pyridine
(106) (R,S)-2-methoxy-8-methyl-5-[α-(2'-carboxybiphenyl-4-yl)-α-ethoxy-methyl]imidazo[1,2-a]pyridine
(107) (R,S)-2-methoxy-8-methyl-5-[α-(2'-carboxybiphenyl-4-yl)-α-n-propyloxy-methyl]imidazo[1,2-a]pyridine
(108) (R,S)-2-methoxy-8-methyl-5-[α-(2'-carboxybiphenyl-4-yl)-α-isobutyloxy-methyl]imidazo[1,2-a]pyridine
(109) (R,S)-2-methoxy-8-methyl-5-[α-(2'-(;H-tetrazol-5-yl)-biphenyl-4-yl)-α-methoxy-methyl]imidazo[1,2-a]pyridine
(110) (R,S)-2-methoxy-8-methyl-5-[α-(2'-carboxybiphenyl-4-yl)-α-propionyloxy-methyl]imidazo[1,2-a]pyridine
(111) (R,S)-2-methoxy-8-methyl-5-[α-(2'-carboxybiphenyl-4-yl)-α-butyryloxy-methyl]imidazo[1,2-a]pyridine
(112) (R,S)-2-methoxy-8-methyl-5-[α-(2'-carboxybiphenyl-4-yl)-α-pivaloyloxy-methyl]imidazo[1,2-a]pyridine
(113) (R,S)-2-methoxy-8-methyl-5-[α-(2'-carboxybiphenyl-4-yl)-α-cyclohexylcarbonyloxy-methyl]imidazo[1,2-a]pyridine
(114) (R,S)-2-methoxy-8-methyl-5-[α-(2'-carboxybiphenyl-4-yl)-α-benzoyloxy-methyl]imidazo[1,2-a]pyridine
(115) (R,S)-2-methoxy-8-methyl-5-[α-(2'-carboxybiphenyl-4-yl)-α-phenylmethylcarbonyloxy-methyl]imidazo[1,2-a]pyridine
(116) (R,S)-2-methoxy-8-methyl-5-[α-(2'-(1H-tetrazol-5-yl)-biphenyl-4-yl)-α-pivaloyloxy-methyl]imidazo[1,2-a]pyridine
(117) (R,S)-2-methoxy-8-methyl-5-[α-(2'-carboxybiphenyl-4-yl)-α-(n-butylamino-carbonyloxy)methyl]imidazo[1,2-a]pyridine
(118) (R,S)-2-methoxy-8-methyl-5-[α-(2'-carboxybiphenyl-4-yl)-α-(phenylamino-carbonyloxy)methyl]imidazo[1,2-a]pyridine
(119) (R,S)-2-methoxy-8-methyl-5-[α-(2'-carboxybiphenyl-4-yl)-α-(cyclohexylamino-carbonyloxy)methyl]imidazo[1,2-a]pyridine
(120) (R,S)-2-methoxy-8-methyl-5-[α-(2'-carboxybiphenyl-4-yl)-α-(benzylamino-carbonyloxy)methyl]imidazo[1,2-a]pyridine
(121) 2-methoxy-8-methyl-5-[(2'-(1H-tetrazol-5-yl)biphenyl-4-yl)methyl]imidazo[1,2-a]pyridine
(122) (R,S)-2-methoxy-8-methyl-5-[α-(2'-(1H-tetrazol-5-yl)-biphenyl-4-yl)-α-(cyclohexylaminocarbonyloxy)methyl]imidazo[1,2-a]pyridine
(123) (R,S)-2-ethoxy-3,8-dimethyl-5-[α-(2'-carboxybiphenyl-4-yl)-α-hydroxy-methyl]imidazo[1,2-a]pyridine
(124) (R,S)-2-ethoxy-3-bromo-8-methyl-5-[α-(2'-carboxybiphenyl-4-yl)-α-hydroxy-methyl]imidazo[1,2-a]pyridine
(125) (R,S)-2-ethoxy-7-methyl-5-[α-(2'-carboxybiphenyl-4-yl)-α-hydroxy-methyl]imidazo[1,2-a]pyridine
(126) (R,S)-2-ethoxy-6-methyl-5-[α-(2'-carboxybiphenyl-4-yl)-α-hydroxy-methyl]imidazo[1,2-a]pyridine
(127) (R,S)-2-ethoxy-6,8-dimethyl-5-[α-(2'-carboxybiphenyl-4-yl)-α-hydroxy-methyl]imidazo[1,2-a]pyridine
(128) (R,S)-2-ethoxy-7-trifluoromethyl-5-[α-(2'-carboxybiphenyl-4-yl)-α-hydroxy-methyl]imidazo[1,2-a]pyridine
(129) (R,S)-2-ethoxy-6,8-dimethyl-5-[α-(2'-(1H-tetrazol-5-yl)biphenyl-4-yl)-α-hydroxy-methyl]imidazo[1,2-a]pyridine
(130) (R,S)-2-ethoxy-8-methyl-5-[α-(2'-(1H-tetrazol-5-yl)-biphenyl-4-yl)-α-hydroxy-methyl]imidazo[1,2-a]pyridine
(131) (R,S)-2-ethoxy-8-methyl-5-[α-(2'-carboxybiphenyl-4-yl)-α-ethoxy-methyl]imidazo[1,2-a]pyridine
(132) (R,S)-2-ethoxy-8-methyl-5-[α-(2'-carboxybiphenyl-4-yl)-α-n-propyloxy-methyl]imidazo[1,2-a]pyridine
(133) (R,S)-2-ethoxy-8-methyl-5-[α-(2'-carboxybiphenyl-4-yl)-α-isobutyloxy-methyl]imidazo[1,2-a]pyridine
(134) (R,S)-2-ethoxy-8-methyl-5-[α-(2'-(1H-tetrazol-5-yl)-biphenyl-4-yl)-α-methoxy-methyl]imidazo[1,2-a]pyridine
(135) (R,S)-2-ethoxy-8-methyl-5-[α-(2'-carboxybiphenyl-4-yl)-α-propionyloxy-methyl]imidazo[1,2-a]pyridine
(136) (R,S)-2-ethoxy-8-methyl-5-[α-(2'-carboxybiphenyl-4-yl)-α-butyryloxy-methyl]imidazo[1,2-a]pyridine
(137) (R,S)-2-ethoxy-8-methyl-5-[α-(2'-carboxybiphenyl-4-yl)-α-pivaloyloxy-methyl]imidazo[1,2-a]pyridine
(138) (R,S)-2-ethoxy-8-methyl-5-[α-(2'-carboxybiphenyl-4-yl)-α-cyclohexylcarbonyloxy-methyl]imidazo[1,2-a]pyridine
(139) (R,S)-2-ethoxy-8-methyl-5-[α-(2'-carboxybiphenyl-4-yl)-α-benzoyloxy-methyl]imidazo[1,2-a]pyridine
(140) (R,S)-2-ethoxy-8-methyl-5-[α-(2'-carboxybiphenyl-4-yl)-α-phenylmethylcarbonyloxy-methyl]imidazo[1,2-a]pyridine
(141) (R,S)-2-ethoxy-8-methyl-5-[α-(2'-(1H-tetrazol-5-yl)-biphenyl-4-yl)-α-pivaloyloxy-methyl]imidazo[1,2-a]pyridine
(142) (R,S)-2-ethoxy-8-methyl-5-[α-(2'-carboxybiphenyl-4yl)-α-(n-butylamino-carbonyloxy)methyl]imidazo[1,2-a]pyridine
(143) (R,S)-2-ethoxy-8-methyl-5-[α-(2'-carboxybiphenyl-4-yl)-α-(phenylamino-carbonyloxy)methyl]imidazo[1,2-a]pyridine
(144) (R,S)-2-ethoxy-8-methyl-5-[α-(2'-carboxybiphenyl-4-yl)-α-(cyclohexylamino-carbonyloxy)methyl]imidazo[1,2-a]pyridine
(145) (R,S)-2-ethoxy-8-methyl-5-[α-(2'-carboxybiphenyl-4-yl)-α-(benzylamino-carbonyloxy)methyl]imidazo[1,2-a]pyridine
(146) 2-ethoxy-8-methyl-5-[(2'-(1H-tetrazol-5-yl) biphenyl-4-yl)methyl]imidazo[1,2-a]pyridine
(147) (R,S)-2-ethoxy-8-methyl-5-[α-(2'-(1H-tetrazol-5-yl)-biphenyl-4-yl)-α-(cyclohexylaminocarbonyloxy)methyl]imidazo[1,2-a]pyridine (148) (R,S)-2-ethyl-3-carboxy-8-methyl-5-[α-(2'-carboxybiphenyl-4-yl)-α-hydroxy-methyl]imidazo[1,2-a]pyridine (149) (R,S)-2-ethyl-3-ethoxycarbonyl-8-methyl-5-[α-(2'-carboxybiphenyl-4-yl)-α-hydroxy-methyl]imidazo[1,2-a]pyridine (150) (R,S)-2-n-propyl-3-carboxy-8-methyl-5-[α-(2'-carboxy-biphenyl-4-yl)-α-hydroxy-methyl]imidazo[1,2-a]pyridine (151) (R,S)-2-n-propyl-3-ethoxycarbonyl-8-methyl-5-[α-(2'-carboxybiphenyl-4-yl)-α-hydroxy-methyl]imidazo[1,2-a]pyridine (152) (R,S)-2-cyclopropyl-3-carboxy-8-methyl-5-[α-(2'-carboxybiphenyl-4-yl)-α-hydroxy-methyl]imidazo[1,2-a]pyridine (153) (R,S)-2-cyclopropyl-3-ethoxycarbonyl-8-methyl-5-[α-(2'-carboxybiphenyl-4-yl)-α-hydroxy-methyl]imidazo[1,2-a]pyridine (154) (R,S)-2-n-butyl-3-carboxy-8-methyl-5-[α-(2'-carboxy-biphenyl-4-yl)-α-hydroxy-methyl]imidazo[1,2-a]pyridine (155) (R,S)-2-n-butyl-3-ethoxycarbonyl-8-methyl-5-[α(2'-carboxybiphenyl-4-yl)-α-hydroxy-methyl]imidazo[1,2-a]pyridine (156) (R,S)-2-methoxy-3-carboxy-8-methyl-5-[α-(2'-carboxy-biphenyl-4-yl)-α-hydroxy-methyl]imidazo[1,2-a]pyridine (157) (R,S)-2-methoxy-3-ethoxycarbonyl-8-methyl-5-[α-(2'-carboxybiphenyl-4-yl)-α-hydroxy-methyl]imidazo[1,2-a]pyridine (158) (R,S)-2-ethoxy-3-carboxy-8-methyl-5-[α-(2'-carboxybiphenyl-4-yl)-α-hydroxy-methyl]imidazo[1,2 a]pyridine (159) (R,S)-2-ethoxy-3-ethoxycarbonyl-8-methyl-5-[α-(2'-carboxybiphenyl-4-yl)-α-hydroxy-methyl]imidazo[1,2-a]pyridine In the Examples of Pharmaceutical Formulations which follow, any suitable compound of formula I, particularly those compounds wherein Re represents a carboxy or 1H-tetrazolyl group, may be used as the active substance:

EXAMPLE I

| Ampoules containing 50 mg of active substance per 5 ml | |
|---|---|
| Active substance | 50 mg |
| KH$_2$PO$_4$ | 2 mg |
| Na$_2$HPO$_4$ × 2H$_2$O | 50 mg |
| NaCl | 12 mg |
| Water for injections ad | 5 ml |

Preparation

The buffer substances and isotonic substance are dissolved in some of the water. The active substance is added and, once it has been completely dissolved, water is added to make up the required volume.

EXAMPLE II

| Ampoules containing 100 mg of active substance per 5 ml | |
|---|---|
| Active substance | 100 mg |
| Methyl glucamine | 35 mg |
| Glycofurol | 1000 mg |
| Polyethyleneglycol-polypropyleneglycol block polymer | 250 mg |
| Water for injections ad | 5 ml |

Preparation

Methyl glucamine is dissolved in some of the water and the active substance is dissolved with stirring and heating. After the addition of solvents, water is added to make up the desired volume.

EXAMPLE III

| Tablets containing 50 mg of active substance | |
|---|---|
| Active substance | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation

The active substance, CaHPO$_4$, lactose and corn starch are uniformly moistened with an aqueous PVP solution. The mass is passed through a 2 mm screen, dried at 50° C. in a circulating air dryer and screened again.

After the lubricant has been added, the granules are compressed in a tablet making machine.

EXAMPLE IV

| Coated tablets containing 50 mg of active substance | |
|---|---|
| Active substance | 50.0 mg |
| Lysine | 25.0 mg |
| Lactose | 60.0 mg |
| Corn starch | 34.0 mg |
| Gelatin | 10.0 mg |
| Magnesium stearate | 1.0 mg |
| | 180.0 mg |

Preparation

The active substance is mixed with the excipients and moistened with an aqueous gelatin solution. After screening and drying the granules are mixed with magnesium stearate and compressed to form tablet cores.

The cores thus produced are covered with a coating by known methods. A colouring may be added to the coating suspension or solution.

EXAMPLE V

| Coated tablets containing 100 mg of active substance | |
|---|---|
| Active substance | 100.0 mg |
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |
| Magnesium stearate | 1.2 mg |
| | 350.0 mg |

Preparation

The active substance is mixed with the excipients and moistened with an aqueous PVP solution. The moist mass is passed through a 1.5 mm screen and dried at 45° C. After drying, it is screened again and the magnesium stearate is added. This mixture is compressed into cores.

The cores thus produced are covered with a coating by known methods. Colourings may be added to the coating suspension or solution.

EXAMPLE VI

| Capsules containing 250 mg of active substance | |
|---|---|
| Active substance | 250.0 mg |
| Corn starch | 68.5 mg |
| Magnesium stearate | 1.5 mg |
| | 320.0 mg |

Preparation

The active substance and corn starch are mixed together and moistened with water. The moist mass is screened and dried. The dry granules are screened and mixed with magnesium stearate. The final mixture is packed into size 1 hard gelatin capsules.

EXAMPLE VII

| Oral suspension containing 50 mg of active substance per 5 ml | |
|---|---|
| Active substance | 50.0 mg |
| Hydroxyethylcellulose | 50.0 mg |
| Sorbic acid | 5.0 mg |
| 70% sorbitol | 600.0 mg |
| Glycerol | 200.0 mg |
| Flavouring | 15.0 mg |
| Water ad | 5.0 ml |

Preparation

Distilled water is heated to 70° C. Hydroxyethylcellulose is dissolved therein with stirring. With the addition of sorbitol solution and glycerol the mixture is cooled to ambient temperature. At ambient temperature, sorbic acid, flavouring and active substance are added. The suspension is evacuated with stirring to remove any air. One dose of 50 mg is contained in 5.0 ml.

EXAMPLE VIII

| Suppositories containing 100 mg of active substance | |
|---|---|
| Active substance | 100.0 mg |
| Solid fat | 1600.0 mg |
| | 1700.0 mg |

Preparation

The hard fat is melted. At 40° C. the ground active substance is homogeneously dispersed in the melt. It is cooled to 38° C. and poured into slightly chilled suppository moulds.

What is claimed is:
1. An imidazo[1,2-a]pyridine of the formula

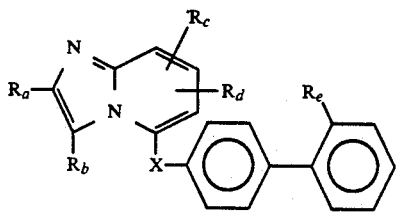

(I)

wherein
- $R_a$ denotes a straight-chained or branched $C_{1-6}$-alkyl group, a cycloalkyl group, an alkyl group substituted by an alkoxy group, or a $C_{1-4}$-alkoxy group,
- $R_b$ denotes a hydrogen, fluorine, chlorine or bromine atom, or an alkyl, hydroxymethyl, trifluoromethyl, formyl, carboxy, alkoxycarbonyl, cyano, nitro, $NH_2CH_2-$, $R_1NHCH_2-$ or $R_1NR_2CH_2-$ group, wherein
  - $R_1$ and $R_2$, which may be identical or different, denote $C_{1-6}$-alkyl groups, cycloalkyl, cycloalkylalkyl, phenyl or phenylalkyl groups or
  - $R_1$ and $R_2$ together denote a $C_{4-6}$-n-alkylene group,
- $R_c$ denotes a hydrogen, fluorine, chlorine or bromine atom, an alkyl group optionally substituted by an alkoxy or phenylalkoxy group, an alkoxy, phenylalkoxy, trifluoromethyl, $H_2N-$, $R_1NH-$ or $R_1NR_2-$ group, wherein $R_1$ and $R_2$ are as hereinbefore defined,
- $R_d$ denotes a hydrogen atom or an alkyl group,
- $R_e$ denotes a carboxy group, a group which may be converted in vivo into a carboxy group, or a cyano, 1H-tetrazolyl, 1-triphenylmethyl-tetrazolyl, alkanesulphonylaminocarbonyl, phenylsulphonylaminocarbonyl, phenylalkanesulphonylaminocarbonyl, trifluoromethanesulphonylaminocarbonyl, phosphino, O-alkyl-phosphino, O-aralkyl-phosphino, phosphono, O-alkyl-phosphono, O-aralkyl-phosphono, O,O-dialkyl-phosphono, phosphono-methyl, O-alkyl-phosphonomethyl, O-aralkyl-phosphono-methyl, O-aryl-phosphono-methyl, O,O-dialkyl-phosphonomethyl, phosphato, O-alkyl-phosphato, O-aralkyl-phosphato, O-aryl-phosphato or O,O-dialkyl-phosphoryl group,
- X denotes an oxygen atom, an imino group optionally substituted by a formyl, $R_1-$ or $R_1CO-$ group, or a $-CO-$, $-(HON=C)-$ or $-(R_3CR_4)-$ group, wherein
  - $R_3$ is a hydrogen atom or an alkyl group and
  - $R_4$ is a hydrogen atom, an alkoxy group substituted by a carboxy, alkoxycarbonyl, aminocarbonyl, alkylaminocarbonyl, dialkylaminocarbonyl or heteroaryl group, wherein the heteroaryl group is linked to the alkoxy group via a carbon-carbon bond,
  - an alkoxy group substituted in the 2, 3 or 4-position by a heteroaryl group, wherein the heteroaryl group is linked to the alkoxy group via a carbon-nitrogen bond,
  - a hydroxy, dialkylphosphonomethoxy, azido, $CHO-O-$, $R_1O-$, $R_5NR_6-$, $R_1CO-O-$, $R_1O-CO-O-$, $CHO-NR_5-$, $R_1-CO-NR_7-$, $R_1O-CO-NR_5-$, $R_5NR_6-CO-O-$, $R_1SO_2-O-$, $R_5NR_6-CO-NR_5-$ or $R_1SO_2-NR_7-$ group or
  - $R_3$ and $R_4$ together denote a 1,2-ethylenedioxy- or 1,3-n-propylenedioxy group,
- wherein in the above-mentioned groups, $R_1$ is as hereinbefore defined,
- $R_5$ and $R_6$, which may be identical or different, represent hydrogen atoms or have the meanings given for $R_1$ and $R_2$ hereinbefore,
- $R_7$ denotes a hydrogen atom or an alkyl group or $R_1$ and $R_7$ together denote a $C_{3-5}$-n-alkylene group,
- wherein, unless otherwise specified, an alkyl or alkoxy moiety mentioned above may contain 1 to 4 carbon atoms and a cycloalkyl moiety mentioned above may contain 3 to 7 carbon atoms, and the term "an aryl group" denotes a phenyl group optionally mono or disubstituted by a fluorine, chlorine or bromine atom, or by a hydroxy, alkyl, alkoxy, phenylalkoxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylaminosulphonyl or dialkylaminosulphonyl group, wherein each alkyl moiety may contain 1 to 4 carbon atoms, or a naphthyl group and the term "heteroaryl group" denotes a 5-membered heteroaromatic ring, bound via a carbon atom or an imino group, and containing an imino group, an oxygen or sulphur atom or an imino group and an oxygen, sulphur or nitrogen atom, or denotes a 6-membered heteroaromatic ring bound via a carbon atom and containing 1 or 2 nitrogen atoms, whilst the above-mentioned heteroaromatic rings may be substituted in the carbon skeleton by a $C_{1-6}$-alkyl group or by a phenylalkyl group and there may be attached to both the 5-membered and to the 6-membered heteroaromatic rings, in each case via two adjacent carbon atoms, an n-propylene, n-butylene or 1,3-butadienyl group or, via an imino group and an adjacent carbon atom, an n-butylene or 1,3-butadienyl group, and in an anellated pyridine ring thus formed a methine group may be replaced by a nitrogen atom and a vinylene group in the 3-, 4-position relative to the nitrogen atom of the pyridine ring formed may be replaced by a sulphur atom or in an anellated phenyl ring thus formed one or two methine groups may be replaced by N-atoms, whilst additionally the above-mentioned fused-on aromatic or heteroaromatic rings in the carbon skeleton may be monosubstituted by a fluorine, chlorine or bromine atom, or by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, fluoromethyl, difluoromethyl, trifluoromethyl, alkanoyl, aminosulphonyl, alkylaminosulphonyl or dialkylaminosulphonyl group or disubstituted by fluorine or chlorine atoms or by methyl, methoxy or hydroxy groups, and two methyl substituents in the 1,2-position relative to one another may be linked to one another by a methylene or ethylene bridge and an NH group optionally present in an imidazole ring may be substituted by a $C_{1-6}$-alkyl group, by a phenylalkyl group or by a cycloalkyl group, or an enantiomer or salt thereof.

2. An imidazo[1,2-a]pyridine as recited in claim 1, wherein $R_a$ denotes a straight-chained or branched $C_{1-4}$-alkyl group, a cyclopropyl, cyclobutyl, alkoxy, methoxymethyl or ethoxymethyl group, $R_b$ denotes a hydrogen, chlorine or bromine atom, an alkyl, aminomethyl, $R_1NHCH_2$ or $R_1NR_2CH_2$ group, wherein $R_1$ and $R_2$, which may be identical or different, denote $C_{1-4}$-alkyl groups, cyclohexyl, phenyl or benzyl groups or $R_1$ and $R_2$ together denote an n-butylene group, $R_c$ denotes a hydrogen, chlorine or bromine atom, an alkyl or trifluoromethyl group, $R_d$ denotes a hydrogen atom or an alkyl group, $R_e$ denotes a carboxy or a 1H-tetrazol-5-yl group, X denotes an oxygen atom, an imino group optionally substituted by a formyl, $R_1$ or $R_1CO$ group, or a CO, —(HON=C)— or ($R_3CR_4$) group, wherein $R_3$ denotes a hydrogen atom or an alkyl group and $R_4$ denotes a hydrogen atom, an alkoxy group substituted by a carboxy, alkoxycarbonyl, aminocarbonyl, alkylaminocarbonyl, dialkylaminocarbonyl or heteroaryl group, wherein the heteroaryl group is linked to the alkoxy group via a carbon-carbon bond, an alkoxy group substituted in the 2, 3 or 4-position by a heteroaryl group, wherein the heteroaryl group is linked to the alkoxy group via a carbon-nitrogen bond, a hydroxy, $R_1O$—, $R_1CO$—O—, $R_1O$—CO—O—, azido, $R_5NR_6$—, CHO—$NR_5$—, $R_1$—CO—$NR_7$—, $R_1O$—CO—$NR_5$—, $R_5NR_6$—CO—O—, $R_1SO_2$—O—, $R_5NR_6$—CO—$NR_5$— or $R_1SO_2$—$NR_7$— group, wherein in the abovementioned groups, $R_1$ is as hereinbefore defined, $R_5$ and $R_6$, which may be identical or different, denote hydrogen atoms or have the meanings given for $R_1$ hereinbefore, $R_7$ denotes a hydrogen atom or an alkyl group or $R_1$ and $R_7$ together denote a $C_{3-5}$-n-alkylene group, whilst unless otherwise specified an alkyl or alkoxy moiety mentioned above may contain 1 to 3 carbon atoms and a cycloalkyl moiety mentioned above may contain 3 to 7 carbon atoms, or an enantiomer or salt thereof.

3. An imidazo[1,2-a]pyridine as recited in claim 1, wherein $R_a$ denotes a $C_{2-4}$-alkyl group, $R_b$ denotes a hydrogen atom, $R_c$ denotes a hydrogen atom or a methyl group, $R_d$ denotes a hydrogen atom, $R_e$ denotes a carboxy or 1H-tetrazolyl group and X denotes a carbonyl group or a methylene group optionally substituted by a hydroxy, methoxy, benzyloxy, pyridylmethoxy, acetoxy, ethoxycarbonylmethoxy, cyclohexyl carbonyloxy or cyclohexylaminocarbonyloxy group, or an enantiomer or a salt thereof.

4. An imidazo[1,2-a]pyridine as recited in claim 1, selected from the group consisting of:

(a) (R,S)-2-ethyl-8-methyl-5-[α-(2'-carboxybiphenyl-4-yl)-α-hydroxy-methyl]imidazo[1,2-a]pyridine, (b) (R,S)-2-ethyl-8-methyl-5-[α-(2'-carboxybiphenyl-4-yl)-α-acetoxy-methyl]imidazo[1,2-a]pyridine, (c) (R,S)-2-ethyl-8-methyl-5-[α-(2'-carboxybiphenyl-4-yl)-α-cyclohexylaminocarbonyloxy-methyl]imidazo[1,2-a]pyridine, (d) (R,S)-2-n-propyl-8-methyl-5-[α-(2'-carboxybiphenyl-4-yl)-α-hydroxy-methyl]imidazo[1,2-a]pyridine, an enantiomer, and a salt thereof.

5. A pharmaceutical composition useful for treating a condition treatable by an angiotensin antagonist comprising a therapeutically effective amount of an imidazo[1,2-a]pyridine as recited in claim 1 and one or more inert carriers or diluents.

6. A pharmaceutical composition useful for treating a condition treatable by an angiotensin antagonist comprising a therapeutically effective amount of an imidazo[1,2-a]pyridine as recited in claim 2 and one or more inert carriers or diluents.

7. A pharmaceutical composition useful for treating a condition treatable by an angiotensin antagonist comprising a therapeutically effective amount of an imidazo[1,2-a]pyridine as recited in claim 3 and one or more inert carriers or diluents.

8. A pharmaceutical composition useful for treating a condition treatable by an angiotensin antagonist comprising a therapeutically effective amount of an imidazo[1,2-a]pyridine as recited in claim 4 and one or more inert carriers or diluents.

9. A method for treating a patient suffering from a condition treatable by an angiotensin anatgonist, which comprises administering to the patient a therapeutically effective amount of an imidazo[1,2-a]pyridine as recited in claim 1.

10. A method for treating a patient suffering from a condition treatable by an angiotensin anatgonist, which comprises administering to the patient a therapeutically effective amount of an imidazo[1,2-a]pyridine as recited in claim 2.

11. A method for treating a patient suffering from a condition treatable by an angiotensin anatgonist, which comprises administering to the patient a therapeutically effective amount of an imidazo[1,2-a]pyridine as recited in claim 3.

12. A method for treating a patient suffering from a condition treatable by an angiotensin anatgonist, which comprises administering to the patient a therapeutically effective amount of an imidazo[1,2-a]pyridine as recited in claim 4.

* * * * *